United States Patent
Kullok et al.

(10) Patent No.: US 9,691,289 B2
(45) Date of Patent: Jun. 27, 2017

(54) MONOTONOUS GAME-LIKE TASK TO PROMOTE EFFORTLESS AUTOMATIC RECOGNITION OF SIGHT WORDS

(75) Inventors: Jose Roberto Kullok, Efrat (IL); Saul Kullok, Efrat (IL)

(73) Assignee: Brightstar Learning, Jerusalem (IL)

( * ) Notice: Subject to any disclaimer, the term of this patent is extended or adjusted under 35 U.S.C. 154(b) by 981 days.

(21) Appl. No.: 13/326,675

(22) Filed: Dec. 15, 2011

(65) Prior Publication Data

US 2012/0164618 A1 Jun. 28, 2012

Related U.S. Application Data

(60) Provisional application No. 61/425,845, filed on Dec. 22, 2010, provisional application No. 61/429,265, (Continued)

(51) Int. Cl.
*G09B 19/00* (2006.01)
*G09B 23/28* (2006.01)
(Continued)

(52) U.S. Cl.
CPC ............. *G09B 5/00* (2013.01); *A61B 5/0022* (2013.01); *A61B 5/0484* (2013.01); *A61B 5/16* (2013.01);
(Continued)

(58) Field of Classification Search
CPC ...... G09B 17/00; G09B 17/02; G09B 17/003; G09B 17/04; G09B 17/006; G09B 19/00;
(Continued)

(56) References Cited

U.S. PATENT DOCUMENTS

| 4,195,626 A | * | 4/1980 | Schweizer | ............. | 600/587 |
| 4,770,636 A | * | 9/1988 | Buschke | ............. | 434/236 |

(Continued)

OTHER PUBLICATIONS

Andersen, R.A., "Visual and eye movement functions of the posterior parietal cortex," *An Rev Neurosci* 12:377-403, Annual Review Inc., United States (1989).

(Continued)

*Primary Examiner* — Nikolai A Gishnock
(74) *Attorney, Agent, or Firm* — Sterne, Kessler, Goldstein & Fox P.L.L.C.

(57) ABSTRACT

System and methods are provided to promote effortless automatic recognition of common sight words. A subject performs a game-like task that generates novel non-verbal visual stimuli that triggers visual attention shifts that enhance foveal and parafoveal recognition of non-verbal and verbal stimuli laterally presented in the right or left visual field. The present invention engages a shared motor-perceptual-cognitive neural network involving oculomotor, visuomotor and selective executive cognitive behaviors on both brain hemispheres. The present invention has applications to a wide range of non-verbal pre-orthographic visual processes and early lexical processes, not only contributing to enabling reading fluency to dyslexics, reluctant and slow readers, but also to beginning readers. The present invention has wide applications in learning disabilities and normative individuals learning to read.

78 Claims, 11 Drawing Sheets

Related U.S. Application Data filed on Jan. 3, 2011, provisional application No. 61/524,887, filed on Aug. 18, 2011.

(51) Int. Cl.

| | |
|---|---|
| *A61B 5/16* | (2006.01) |
| *G09B 5/00* | (2006.01) |
| *A61B 5/0484* | (2006.01) |
| *A61B 5/00* | (2006.01) |
| *A61B 6/00* | (2006.01) |
| *G09B 19/04* | (2006.01) |
| *A61B 8/00* | (2006.01) |
| *A61B 8/08* | (2006.01) |
| *G09B 17/00* | (2006.01) |
| *G09B 19/06* | (2006.01) |

(52) U.S. Cl.
CPC ............ *A61B 5/162* (2013.01); *A61B 5/4088* (2013.01); *A61B 5/486* (2013.01); *A61B 5/7264* (2013.01); *A61B 5/7267* (2013.01); *A61B 5/7285* (2013.01); *A61B 6/541* (2013.01); *A61B 8/0808* (2013.01); *A61B 8/543* (2013.01); *G09B 17/003* (2013.01); *G09B 17/006* (2013.01); *G09B 19/00* (2013.01); *G09B 19/04* (2013.01); *G09B 19/06* (2013.01); *G09B 23/28* (2013.01); *A61H 2230/00* (2013.01); *A61H 2230/04* (2013.01); *A61H 2230/06* (2013.01); *A61H 2230/10* (2013.01); *Y10S 128/905* (2013.01); *Y10S 128/92* (2013.01)

(58) Field of Classification Search
CPC . G09B 7/02; G09B 7/04; G09B 23/28; G09B 5/00; G09B 5/02; G09B 5/04; G09B 5/06; G09B 5/065; G09B 19/04; G09B 19/06; A61B 5/16; A61B 5/4088; A61B 5/486; A61B 5/7264; A61B 5/0484; A61B 5/0022; A61B 5/162; A61B 5/7267; A61B 5/7285; A61B 5/541; A61B 8/0808; A61B 8/543; A61H 2230/00; A61H 2230/04; A61H 2230/06; A61H 2230/10; Y10S 128/92; Y10S 128/905
USPC ......................................................... 434/236
See application file for complete search history.

(56) References Cited

U.S. PATENT DOCUMENTS

| | | | | |
|---|---|---|---|---|
| 5,230,629 A * | 7/1993 | Buschke | .................... | 434/236 |
| 5,295,491 A * | 3/1994 | Gevins | .................... | 600/544 |
| 5,487,671 A * | 1/1996 | Shpiro et al. | .................... | 434/185 |
| 5,720,619 A * | 2/1998 | Fisslinger | .................... | 434/336 |
| 5,724,987 A * | 3/1998 | Gevins et al. | .................... | 600/544 |
| 5,807,114 A * | 9/1998 | Hodges et al. | .................... | 434/236 |
| 5,900,567 A * | 5/1999 | Fay | .................... | G10H 1/0025 84/609 |
| 6,045,515 A * | 4/2000 | Lawton | .................... | A61B 3/022 351/223 |
| 6,213,956 B1 * | 4/2001 | Lawton | .................... | A61B 3/022 351/223 |
| 6,226,595 B1 * | 5/2001 | Rossi | .................... | G01V 3/38 702/10 |
| 6,293,904 B1 * | 9/2001 | Blazey et al. | .................... | 600/26 |
| 6,306,086 B1 * | 10/2001 | Buschke | .................... | 600/300 |
| 6,328,569 B1 * | 12/2001 | Jenkins et al. | .................... | 434/169 |
| 6,425,764 B1 * | 7/2002 | Lamson | .................... | 434/236 |
| 6,457,362 B1 * | 10/2002 | Wright et al. | .................... | 73/585 |
| 6,457,975 B1 * | 10/2002 | Miranda et al. | .................... | 434/236 |
| 6,511,324 B1 * | 1/2003 | Wasowicz | .................... | 434/167 |
| 6,520,905 B1 * | 2/2003 | Surve et al. | .................... | 600/26 |
| 6,615,197 B1 * | 9/2003 | Chai | .................... | 706/14 |
| 6,644,976 B2 * | 11/2003 | Kullok et al. | .................... | 434/236 |
| 6,662,032 B1 * | 12/2003 | Gavish et al. | .................... | 600/323 |
| 6,689,058 B2 * | 2/2004 | Buschke | .................... | 600/300 |
| 6,980,207 B2 * | 12/2005 | Yamamoto | .................... | A63F 13/08 345/419 |
| 7,070,563 B2 * | 7/2006 | Buschke | .................... | 600/300 |
| 7,122,004 B1 * | 10/2006 | Cassily | .................... | A61B 5/162 434/258 |
| 7,309,315 B2 * | 12/2007 | Kullok et al. | .................... | 600/558 |
| 7,314,444 B2 * | 1/2008 | Buschke | .................... | 600/300 |
| 7,589,727 B2 * | 9/2009 | Haeker | .................... | G10H 1/0008 345/440 |
| 7,678,047 B2 * | 3/2010 | Shiomi | .................... | A61B 5/00 600/300 |
| 8,070,572 B2 * | 12/2011 | Lee | .................... | G09B 9/00 463/7 |
| 8,308,539 B1 * | 11/2012 | Cleghorn | .................... | 463/11 |
| 8,506,374 B1 * | 8/2013 | Cleghorn | .................... | 463/11 |
| 8,676,997 B2 * | 3/2014 | Rapo | .................... | A63F 13/12 463/39 |
| 2002/0103429 A1 * | 8/2002 | deCharms | .................... | 600/410 |
| 2004/0072133 A1 * | 4/2004 | Kullok et al. | .................... | 434/236 |
| 2004/0230252 A1 * | 11/2004 | Kullok et al. | .................... | 607/48 |
| 2005/0080592 A1 * | 4/2005 | Buscema | .................... | G09B 5/00 702/182 |
| 2005/0142522 A1 * | 6/2005 | Kullok et al. | .................... | 434/169 |
| 2005/0196735 A1 * | 9/2005 | Buschke | .................... | 434/236 |
| 2007/0060338 A1 * | 3/2007 | Kefaloukos | .................... | A63F 13/005 463/30 |
| 2007/0105073 A1 * | 5/2007 | Kullok et al. | .................... | 434/169 |
| 2007/0166675 A1 * | 7/2007 | Atkins et al. | .................... | 434/236 |
| 2008/0056548 A1 * | 3/2008 | Irarrazaval | .................... | G06T 5/00 382/128 |
| 2009/0024050 A1 * | 1/2009 | Jung et al. | .................... | 600/544 |
| 2010/0033333 A1 * | 2/2010 | Victor | .................... | A61B 5/7264 340/576 |
| 2012/0108909 A1 * | 5/2012 | Slobounov | .................... | A61B 5/1124 600/300 |
| 2014/0004491 A1 * | 1/2014 | Scheidl | .................... | 434/236 |
| 2014/0323190 A1 * | 10/2014 | Hinman | .................... | A61B 5/168 463/9 |
| 2015/0231020 A1 * | 8/2015 | Battin | .................... | A63B 24/0087 601/37 |

OTHER PUBLICATIONS

Andersen, R.A. and Buneo, C.A., "Sensorimotor integration in posterior parietal cortex," *Adv Neurol* 93: 159-177, Lippincott Williams & Wilkins, United States (2003).

Anderson, C.A. and Bushman, B.J., "Effects of violent video games on aggressive behavior, aggressive cognition, aggressive affect, physiological arousal, and prosocial behavior: A meta-analytic review of the scientific literature," *Psychol Sci* 12:353-359, Sage, United States (2001).

Biscaldi M., et al., "Poor saccadic control correlates with dyslexia," *Neuropsychologia* 36:1189-1202, Elsevier Science Ltd., England (1998).

Bisley, J.W., and Goldberg, M.E., "Neuronal activity in the lateral intraparietal area and spatial attention", *Science* 299:81-86, American Association for the Advancement of Science, United States (2003a).

Bisley, J.W., and Goldberg, M.E., "The role of the parietal cortex in the neural processing of saccadic eye movements," *Adv Neurol* 93: 141-157, Lippincott Williams & Wilkins, United States (2003b).

Blau, V., et al., "Reduced Neural Integration of Letters and Speech Sounds Links Phonological and Reading Deficits in Adult Dyslexia," *Curr Biol* 19(6):503-508, Cell Press, United States (2009).

Brainerd, C.J., and Reyna, V.F., "Memory independence and memory interference in cognitive development", *Psychol Rev* 100:42-67, American Psychological Association, United States (1993).

Brannan, J., and Williams, M., "Allocation of visual attention in good and poor readers", *Percept Psychophys* 41:23-28, Psychonomic Society, United States (1987).

(56) References Cited

OTHER PUBLICATIONS

Cao, F., et al., "Deficient Orthographic and phonological representations in children with dyslexia revealed by brain activation patters," *J Child Psychol Psychiatry* 47(10):1041-1050, Blackwell Publishers, England (2006).
Case, R., "Validation of a neo-Piagetian mental capacity construct," *J Exp Child Psychol* 14:287-302, Academic Press, United States (1972).
Colby, C.L., "The Neuroanatomy and Neurophysiology of Attention," *J Child Neurol 6 Suppl*:S90-118, Sage, United States (1991).
Coltheart, M., et al., "Models of reading aloud dual-route and parallel-distributed processing approaches," *Psychol Rev* 100:589-608, American Psychological Association, United States (1993).
Corbetta, M., and Shulman, G.L., "Control of goal-directed and stimulus-driven attention in the brain," *Nat Rev Neurosci* 3:201-215, Nature Publishing Group, England (2002).
Corbetta, M., et al., "A common network of functional areas for attention and eye movements" *Neuron* 21:761-773, Cell Press, United States (1998).
Corbetta, M., et al., "A PET study of visuospatial attention," *J Neurosci* 13:1202-1226, Society for Neuroscience, United States (1993).
Critchley, M., *The Parietal Lobes*, Hafner Press, England (1953).
Deubel, H., and Schneider, W., "Saccade target selection and object recognition: evidence for a common attentional mechanism," *Vision Res* 36: 1827-1837, Elsevier Science Ltd., England (1996).
Diamond, A., and Doar, B., "The performance of human infants on a measure of frontal cortex function, the delayed response task," *Dev Psychobiol* 22:271-294, John Wiley and Sons, Inc., United States (1989).
Downar, J., et al., "The effect of task relevance on the cortical response to changes in visual and auditory stimuli: An event-related fMRI study" *Neuroimage* 14: 1256-1267, Academic Press (2001).
Easterbrooke, J.A., "The effect of emotion on cue utilization and the organization of behavior," *Psychol Rev* 66:187-201, American Psychological Association, United States (1959).
Eden, G.F., et al., "Differences in eye movements and reading problems in dyslexic and normal children", *Vision Res* 34:1345-1358, Elsevier Science Ltd., England (1994).
Eden, G.F., et al., "Visuospatial ability and language processing in reading disabled and normal children," In: Wright, S.F., Groner R. (ed) *Studies in visual information processing: facets of dyslexia and its remediation*, pp. 321-335, North-Holland, Netherlands (1993).
Efron, R., "The effect of handedness on the perception of simultaneity and temporal order", *Brain* 86:261-284, Oxford University Press, England (1963).
Ehri, L.C. and McCormick, S., "Phases of word learning: Implications for instruction with delayed and disabled readers," *Read Writ Q* 14: 135-163, Taylor and Francis, United States (1998).
Ehri, L.C., "Grapheme-phoneme knowledge is essential for learning to read words in English". In Metsala, J.L., and Ehri, E.C., (Eds.), *Word recognition in beginning literacy*, pp. 3-40, Erlbaum, United States (1998).
Enroth-Cugell, C. and Robson, J.G., "The contrast sensitivity of retinal ganglion cells in the cat" *J Physiol* 187:517-552, Cambridge University Press, England (1966).
Eysenck, M.W., and Keane, M.T., *Cognitive Psychology: A Student's Handbook* (5th ed.), Psychology Press, United States (2005).
Facoetti, A., "Facilitation and inhibition mechanisms of human visuospatial attention in a non-search task", *Neurosci Lett* 298:45-48, Elsevier Scientific Publishers, Ireland (2001).
Facoetti, A., and Molteni, M., "The gradient of visual attention in developmental dyslexia," *Neuropsychologia* 39:352-357, Elsevier Science Ltd., England (2001).
Facoetti, A., and Turatto, M., "Asymmetrical visual fields distribution of attention in dyslexic children: a neuropsychological study," *Neurosci Lett* 290:216-218, Elsevier Scientific Publishers, Ireland (2000).
Facoetti, A., et al., "Auditory and visual automatic attention deficits in developmental dyslexia," *Cogn Brain Res* 16: 185-191, Elsevier Science Publishers, United States (2003).
Facoetti, A., et al., "The role of visuospatial attention in developmental dyslexia: Evidence from a rehabilitation study," *Cogn Brain Res* 15: 154-164, Elsevier Science Publishers, United States (2003c).
Facoetti, A., et al., "The spatial distribution of visual attention in developmental dyslexia," *Exp Brain Res* 132:531-538, Springer-Verlag, Germany (2000a).
Facoetti, A., et al., "The time course of attentional focusing in dyslexic and normally reading children," *Brain Cogn* 53: 181-184, Academic Press, United States (2003a).
Facoetti, A., et al., "Visual and auditory attentional capture is sluggish in children with developmental dyslexia," *Acta Neurobiol Exp (Wars)* 65: 61-72, Nencki Institute of Experimental Biology, Poland (2005).
Facoetti, A., et al., "Visuospatial attention in developmental dyslexia," *Cortex* 36:109-123, Masson, Italy (2000b).
Facoetti, A., et al., "Visual Spatial Attention and Speech Segmentation are both Impaired in Preschoolers at Familial Risk for Developmental Dyslexia," *Dyslexia* 16(3):226-239, John Wiley and Sons Ltd., United States (2010).
Fowler, M.S., et al., "Orthoptic investigation of neurological patients undergoing rehabilitation," *Br Orthoptic J* 48:2-27, British Orthoptic Society, England (1991).
Geiger, G., et al., "Dyslexic children learn a new strategy for reading: a controlled experiment," *Vision Res* 34:1223-1233, Elsevier Science Ltd., England, (1994).
Giesbrecht, B., et al., "Neural mechanisms of top-down control during spatial and feature attention," *Neuroimage* 19: 496-512, Academic Press, United States (2003).
Goodale, M.A., and Milner, A.D., "Separate visual pathways for perception and action," *Trends Neurosci* 15:20-25, Elsevier Applied Science Publishing, England (1992).
Goodale, M.A., and Milner, A.D., *Sight unseen: An exploration of conscious and unconscious vision*, Oxford University Press, England (2004).
Goodale, M.A., et al., "Two distinct modes of control for object-directed action," *Prog Brain Res* 144: 131-144, Elsevier, Netherlands (2004).
Hari, R. and Koivikko, H., "Left-side mini-neglect and attentional sluggishness in dyslexic adult," *Soc Neurosci Abstr* 25:1634, Society for Neuroscience, United States (1999).
Hari, R., et al., "Left minineglect in dyslexic adults," *Brain* 124:1373-1380, Oxford University Press, England (2001).
Hirsh, I.J., and Sherrick Jr., C.E., "Perceived order in different sense modalities," *J Exp Psychol* 62:423-432, American Psychological Association, United States (1961).
Hoffman, J., and Subramaniam, B., "The role of visual attention in saccadic eye movements," *Percept Psychophys* 57(6):787-795, Psychonomic Society, United States (1995).
Jones, M., et al., "Dyslexic and nondyslexic reading fluency: Rapid automatized naming and the importance of continuous lists," *Psychon Bull Rev* 16(3):567-572, Psychonomic Society, Inc., United States (2009).
Kowler, E., et al., "The role of attention in the programming of saccades," *Vision Res* 35:1897-1916, Elsevier Science Ltd., England (1995).
Laberge, D., "Attentional Control: Brief and prolonged," *Psychol Res* 66:230-233, Springer-Verlag, Germany (2002).
Laberge, D., and Brown, V., "Theory of attentional operations in shape identification," *Psychol Rev* 96:101-124, American Psychological Association, United States (1989).
Laberge, D., and Samuels, S.A., "Toward a theory of automatic information processing in reading," *Cogn Psychol* 6:293-323, Academic Press, United States (1974).
Laberge, D., et al., "Shifting Attention in Visual Space: Tests of Moving-Spotlight Models Versus an Activity-Distribution Model," *J Exp Psychol Hum Percept Perform* 23(5):1380-1392, American Psychological Association, United States (1997).

(56) References Cited

OTHER PUBLICATIONS

Livingstone, M.S., and Hubel, D.H., "Segregation of form, color movement, and depth: anatomy, physiology and perception," *Science* 240:740-749, American Association for the Advancement of Science, United States (1988).
Lovegrove, W., et al., "A theoretical and experimental case for a visual deficit in specific reading disability," *Cogn Neuropsychol* 3(2):225-267, Lawrence Erlbaum Associates Limited, United States (1986).
Maunsell, J.H.R., et al., "Magnocellular and parvocellular contributions to responses in the Middle Temporal Visual Area (MT) of the macaque monkey," *J Neurosci* 10(10):3323-3334, Society for Neuroscience, United States (1990).
May, J., et al., "Temporal Order Judgments in Good and Poor Readers," *Neuropsychologia* 26(6):917-924, Pergamon Press, England (1988).
Merigan, W.H., and Maunsell, J.R., "How parallel are the primate visual pathways?" *Annu Rev Neurosci* 16:369-402, Annual Reviews, Inc., United States (1993).
Meyer, M.S., and Felton, R.H., "Repeated reading to enhance fluency: Old approaches and new direction," *Ann Dyslexia* 49:283-306, International Dyslexia Association, United States (1999).
Milner, A.D., and Goodale, M.A., "Visual pathways to perception and action," In Hicks, T.P., Molotchnikoff, S., and Ono, T., (Eds.), *Prog Brain Res* 95:317-337, Elsevier, Netherlands (1993).
Milner, A.D., and Goodale, M.A., *The Visual Brain in Action* ($2^{nd}$ ed.), Oxford University Press, England (2006).
Milner, A.D., and Goodale, M.A., *The Visual Brain in Action*, Oxford University Press, England (1995).
Mischel W., et al., "Cognitive and attentional mechanisms in delay of gratification," *J Pers Soc Psychol* 21:204-218, American Psychological Association, United States (1972).
Mischel, W., "Theory and research on the antecedents of self-imposed delay of reward," In B. A. Maher (Ed.), *Prog Exp Pers Res* 3:85-132, Academic Press, United States (1966).
Mischel, W., et al., "The nature of adolescent competencies predicted by preschool delay of gratification," *J Pers Soc Psychol* 54:687-696, American Psychological Association, United States (1988).
Mishkin, M., and Ungerleider, L.G., "Contribution of striate inputs to the visuospatial functions of parieto-preoccipital cortex in monkeys," *Behav Brain Res* 6(1): 57-77, Elsevier/North-Holland Biomedical Press, Netherlands (1982).
Morris, R.K., and Rayner, K., "Eye movements in skilled reading: implications for developmental dyslexia," In Stein, J.F. (Ed.) *Vision and visual dyslexia*, pp. 233-242, MacMillan Press, England (1991).
Munakata, Y., "Infant perseveration and implications for object permanence theories: a PDP model of the AB task," *Dev Sci* 1:161-184, Blackwell Publishers, England (1998).
Nobre, A.C., et al., "Functional localization of the system for visuospatial attention using positron emission tomography," *Brain*, 120(Pt 3):515-533, Oxford University Press, England (1997).
Omtzigt, D., et al., "Evidence for magnocellular involvement in the identification of flanked Letters," *Neuropsychologia* 40: 1881-1890, Elsevier Science Ltd., England (2002).
Pavlidis, G., "Do eye movements hold the key to dyslexia!" *Neuropsychologia* 19:57-6, Pergamon Press Ltd., England (1981).
Peterson, M.S., et al., "Covert shifts of attention precede involuntary eye movements," *Percept Psychophys* 66:398-405, Psychonomic Society, United States (2004).
Pierrot-Deseilligny C., et al., "Cortical control of memory-guided saccades in man," *Exp Brain Res* 83(3):607-617, Springer-Verlag, Germany (1991b).
Pierrot-Deseilligny C., et al., "Cortical control of reflexive visually guided saccades," *Brain* 114: 1473-1485, Oxford University Press, England (1991a).
Pierrot-Deseilligny, C., et al., "Cerebral ocular motor signs," *J Neurol* 244: 65-70, Springer-Verlag, Germany (1997).
Pisella, L., et al., "An 'Automatic Pilot' for the hand in human posterior parietal cortex: Toward reinterpreting optic ataxia," *Nat Neurosci* 3: 729-736, Nature Publishing Group, United States (2000).
Pöppel, E., "A hierarchical model of temporal perception," *Trends Cogn Sci* 1: 56-61, Elsevier Science, England (1997).
Posner, M.I., and Cohen, Y., "Components of visual orienting of attention," In Bouma, H., and Bouwhuis, D., (Eds.) *Attention & Performance X*, pp. 531-556, Erlbaum, United States (1984).
Rayner, K., "Eye movements, perceptual span and reading disability," *Ann Dyslexia* 33:163-173, International Dyslexia Association, United States (1983).
Samuels, S.J., "Reading fluency: Its development and assessment," In Farstrup, A.E., and Samuels, S.J., (Eds.) *What research has to say about reading instruction* (3rd ed.), pp. 166-183, International Reading Association, United States (2002).
Shapley, R., and Perry, V.H., "Cat and monkey retinal ganglion cells and their visual functional roles," *Trends Neurosci* 9: 229-235, Elsevier Applied Science Publishing, England (1986).
Shelhamer, M., et al., "Vergence downward can be controlled by audio feedback, and induces downward ocular deviation," *Exp Brain Res* 101:169-172, Springer-Verlag, Germany (1994).
Solman, R.T., and May, J.G., "Spatial Localization Discrepancies: A Visual Deficiency in Poor Readers," *Am J Psychol* 103(2):243-263, University of Illinois Press, United States (1990).
Solman, R.T., et al., "Colour-mediated grouping effects and disabled readers," *Ophthalmic Physiol Opt* 11(4):320-327, Pergamon Press, England (1991).
Sperling, G., and Weichselgartner, E., "Episodic theory of the dynamics of spatial attention," *Psychol Rev* 102: 503-532, American Psychological Association, United States (1995).
Stanovich, K.E., "Word recognition: Changing perspectives," In Barr, R., Kamil, M.L., Mosenthal, P., and Pearson, P.D., (Eds.), *Handbook of reading research* 2:418-452, Longman, United States (1991).
Stein, J., and Glickstein, M., "Role of the cerebellum in visual guidance of movement," *Physiol Rev* 72:972-1017, American Physiological Society, United States (1992).
Stein, J., and Walsh, V., "To see but not to read; the magnocellular theory of dyslexia," *Trends Neurosci* 20:147-152, Elsevier Science Ltd., England (1997).
Stein, J.F., "Representation of Egocentric Space in the Posterior Parietal Cortex," *Q J Exp Physiol* 74(5):583-606, Cambridge University Press, England (1989).
Steinman, B.A., et al., "Transient visual attention is dominated by the magnocellular stream," *Vision Res* 36:589-599, Elsevier Science Ltd., England (1996).
Steinman, S.B., and Steinman, B.A., "Vision and Attention. I: Current Models of Visual Attention," *Optom Vis Sci* 75(2):146-155, Lippincott Williams & Wilkins, United States (1998).
Steinman, S.B., et al., "A Sensory Explanation for Visual Attention Deficits in the Elderly," *Optom Vis Sci* 71(12):743-749, Lippincott Williams & Wilkins, United States (1994).
Swisher, L., and Hirsh, I.J., "Brain damage and the ordering of two temporally successive stimuli," *Neuropsychologia* 10: 137-152, Pergamon Press, England (1972).
Tallal, P., et al., "Language learning impairments: integrating basic science, technology, and remediation," *Exp Brain Re* 123: 210-219, Springer-Verlag, Germany (1998).
Vidyasagar, T.R., "A neuronal model of attentional spotlight: parietal guiding the temporal," *Brain Res Brain Res Rev* 30:66-76, Elsevier Science, Netherlands (1999).
Vidyasagar, T.R., and Pammer, K., "Impaired visual search in dyslexia relates to the role of the magnocellular pathway in attention," *Neuroreport* 10: 1283-1287, Lippincott Williams & Wilkins, England (1999).
Von Steinbüchel, N., et al., "Temporal constraints of perceiving, generating, and integrating information: Clinical indications," *Restor Neurol Neurosci* 14: 167-182, IOS Press, Netherlands (1999a).
Williams, M.C., and Bologna, N.B., "Perceptual Grouping in Good and Poor Readers," *Percept Psychophys* 38(4):367-374, Psychonomic Society, United States (1985).

(56) References Cited

OTHER PUBLICATIONS

Williams, M.C., et al., "The Effects of Spatial Filtering and Contrast Reduction on Visual Search Times in Good and Poor Readers," *Vision Res* 35(2):285-291, Elsevier Science Ltd., England, (1995).

Wolverton, G.S., and Zola, D.A., "The temporal characteristics of visual information extraction during reading" in Rayner, K., (Ed.), *Eye movements in reading: Perceptual and language processes*, pp. 41-51, 1983, Academic Press, United States (1983).

Wright, R.D., and Ward, L.M., *Orienting of attention*, Oxford University Press, England (2008).

Yantis, S., et al., "Transient neural activity in human parietal cortex during spatial attention shifts," *Nat Neurosci* 5: 995-1002, Nature Publishing Group, United States (2002).

International Search Report and Written Opinion for International Application No. PCT/IB2011/003306, European Patent Office, Netherlands, mailed on Jun. 15, 2012.

\* cited by examiner

Parameters Configuration Module 330 Table

| Number | Name | Particulars |
|---|---|---|
| 1 | Total sessions' duration | 660 seconds |
| 2 | ARC segment duration | 84 seconds |
| 3 | Score Computation interval in an ARC | 63 seconds |
| 4 | First Eye-Tracking interval duration (of object #3) | 81 seconds |
| 5 | Default shape of pathway line borders of object #2 | Library #5 |
| 6 | Default shape of mobile object #1 | Library #6 |
| 7 | Default shape of tracked object #3 | Library #7 |
| 8 | Minimal Separation between pathway borders | 3% of horizontal 'x' screen resolution (in pixels) |
| 9 | Default sinusoidal pathway line borders amplitude | Percentage of horizontal 'x' screen resolution – default left 5; Default right 5.5 |
| 10 | Central Window height | Virtual max size of 45% of vertical 'y' screen resolution (in pixels) |
| 11 | Central window width | Virtual max size of 42% of horizontal 'x' screen resolution (in pixels) |
| 12 | Central reference line locations of object #2 | Library #12. Default: equidistant from borders along the pathway |
| 13 | Trajectory of object #1 movement angular orientation in relation of horizontal 'x' screen axis | 0° (default); 8°; 16° |
| 14 | Velocity of eye-tracking task parameter object #3 | +100 pixels/sec |
| 15 | Acceleration of eye-tracking task parameter object #3 | – 30 pixels/sec$^2$ |
| 16 | Separation of tracking ask lines of object #3 movement on the 'y' vertical axis | 5 pixels (for default screen resolution 1680x1050) |
| 17 | Object #1 colors | Default: yellow |
| 18 | Object #3 colors | Default: orange |
| 19 | Background color of pathway inside borders lines | Default: 140 140 140 |
| 20 | Background color of field outside the pathway | Default: green |
| 21 | Default number of ARC segments in first session | 4 |
| 22 | Default number of sessions in a program | 4 |
| 23 | Number of mouse movements rendering an ARC invalid | ≤ 500 |
| 24 | Idle threshold time for an ARC in $CP_2$ | 110 milliseconds |
| 25 | Running time window interval for idle time calculations | 3 seconds (from where % activity is obtained) |
| 26 | Object #1 color turns red if | % activity ≤ 55 |
| 27 | Object #1 color turns blue if | % activity ≥ 70 |
| 28 | frequency x value in % activity calculation | Each 1 second |
| 29 | Idle threshold time for $CP_n$ | 110 – 10 n (of CP in the ARC) |
| 30 | Time interval between Δd measurements | 100 milliseconds |

FIG. 3

Module 240 Challenge Parameter

From Modulus 340

| ARC CP$_x$ Level | CP$_0$ | CP$_1$ | CP$_2$ | CP$_3$ | CP$_4$ | CP$_5$ | CP$_x$ |
|---|---|---|---|---|---|---|---|
| # of Pathways Module in the screen | 1.5 | 1.75 | 1.75 | 2.0 | 2.0 | 2.25 | 2.25 |
| One Module Pathway Module speed (sec) | 3.0 | 2.6 | 2.2 | 1.8 | 1.4 | 1.1 | 0.9 |
| Amplitude Left border (% of 'x' resolution) | 5.0 | 5.25 | 5.5 | 5.5 | 5.75 | 6.0 | 6.25 |
| Amplitude right border (% of 'x' resolution) | 5.5 | 5.8 | 6.0 | 6.0 | 6.3 | 6.5 | 6.8 |
| Rainy Weather | False | False | False | True | True | True | True |
| Foggy Weather | False | False | False | False | False | True | True |
| Shape of Pathway Object #2 (from Library #5) | Default (D) | D | D | D | D | D | D |
| Shape of Object #1 (from Library #6) | Default (D) | D | D | D | D | D | D |
| Shape of Object #3 (from Library #7) | Default (D) | D | D | D | D | D | D |

To ARC segment 'n' Configuration

FIG. 4

Eye Tracking Task Line Trajectories

<u>Taking place Following an ARC's Eye-hand movement coordination task</u>

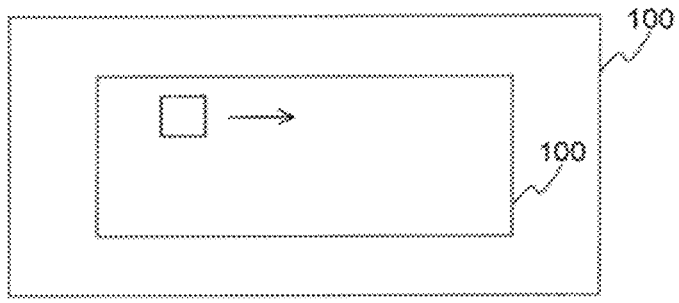

- Higher Eye-Tracking task line trajectory of Object #3 (square icon) in the CW task area. Arrow shows direction of the icon's movement

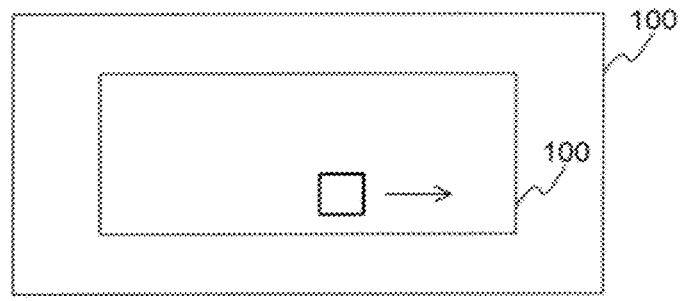

- Lower Eye-Tracking task line trajectory of Object #3 (square icon) in the CW task area. Arrow shows direction of the icon's movement

MONOTONOUS GAME-LIKE TASK TO PROMOTE EFFORTLESS AUTOMATIC RECOGNITION OF SIGHT WORDS

CROSS-REFERENCE TO RELATED APPLICATIONS

This application claims the benefit of U.S. Provisional Patent Application No. 61/425,845, filed Dec. 22, 2010, entitled "SYSTEM FOR MEMORY ENCODING IN CONJUNCTION WITH GAME-LIKE EXERCISES AND METHODS USEFUL IN CONJUNCTION THEREWITH", of U.S. Provisional Patent Application No. 61/429,265, filed Jan. 3, 2011, entitled "IMPROVED SYSTEM FOR MEMORY ENCODING IN CONJUNCTION WITH GAME-LIKE EXERCISES AND METHODS USEFUL IN CONJUNCTION THEREWITH", and of U.S. Provisional Patent Application No. 61/524,887, filed Aug. 18, 2011, entitled "AGILEEYE READER", all of which are incorporated by reference in their entireties herein.

This application is also related to U.S. Pat. No. 7,309,315, issued Dec. 18, 2007, entitled "APPARATUS, METHOD, AND COMPUTER PROGRAM PRODUCT TO FACILITATE ORDINARY VISUAL PERCEPTION VIA AN EARLY PERCEPTUAL-MOTOR EXTRACTION OF RELATIONAL INFORMATION FROM A LIGHT STIMULI ARRAY TO TRIGGER AN OVERALL VISUAL-SENSORY MOTOR INTEGRATION IN A SUBJECT", which is incorporated by reference in its entirety herein.

BACKGROUND OF THE INVENTION

Field of the Invention

The present invention relates generally to visual recognition in human subjects, and, more particularly, to promoting automatic recognition of sight words via generation of non-verbal stimuli that manipulate dyslexics' and poor readers' visual spatial attention.

Background Art

At a first glance, reading seems almost magical: our gaze lands on orthographic signs lying in serial order next to each other, and our brains effortlessly give us access to their meaning and pronunciation. However, reading is far from simple. It is an exceptionally complicated task that involves visual processing and optomotor functions. In order to read, our brain recruits in just about 280 milliseconds, neural networks scattered in many different and distant regions of the cortex across both brain hemispheres.

Reading starts in the central part of the retina, called the fovea, an area dense in high-resolution photoreceptor cells which are sensitive to light. The fovea occupies about 13 degrees of the visual field, and is the only part of the retina that is truly useful for reading. The need for printed text to reach the fovea explains why reading is a dynamic motion task. Our eyes don't sweep a text in a constant fashion, quite the contrary; they sweep a text in small steps/leaps called saccades. Our eyes attain a quasi-stationary state called a fixation that lasts about 220-300 milliseconds for familiar words or up to 500 milliseconds for unfamiliar words. When the eyes fixate, visual information can be extracted and decoded for meaning. During a fixation, the eyes have access to three regions: the foveal, the parafoveal, and the peripheral. The foveal region is the area with the sharpest acuity and includes 2 degrees of visual angle around the point of fixation, where 1 degree is equal to two or three letters (thus, four to six letters are in focus). The parafoveal region extends to about 15-20 letters, and the peripheral region includes everything in the visual field beyond the parafoveal region.

Visual precision is optimal at the center of gaze and gradually decreases towards the periphery since fewer cells are allocated to that portion of the visual scenery. In fact, our perceptual span enables us to identify only about ten or twelve letters per saccade: three or four to the left of the fixation point, and seven or eight to the right of the fixation point. Proficient readers make regressions to text already scanned about 10-15 percent of the time. The main difference between fast and slow readers is that the latter consistently show longer average fixation durations (350-500 milliseconds), shorter saccades, and more frequent regressions. In general, problems in oculomotor control have been considered in poor readers and dyslexics because they show an abnormal pattern of their fixation-saccadic eye movements during reading.

Mainstream scientific research theorizes that many of the reading anomalies observed in developmental dyslexia and in poor readers have been causally linked principally to the Posterior Parietal Cortex (PPC) and magnocellular deficit, but also, to a mild degree, to cerebellar deficits. Indeed, PPC seems to be the 'crossroads of the brain'. See, Critchley M "The Parietal Lobes", London, Hafner Press, (1953). It is generally accepted that the PPC is responsible for (a) sensorimotor integration. See, Goodale M A, Milner A D, "Sight unseen: An exploration of conscious and unconscious vision". Oxford University Press, Oxford-New York, (2004); Milner A D, Goodale M A, "The Visual Brain in Action", Oxford University Press, Oxford, (1995); Pisella L, Grea H, Tilikete C, Vighetto A, Desmurget M, Rode G, Boisson D, Rossetti Y, "An 'Automatic Pilot' for the hand in human posterior parietal cortex: Toward reinterpreting optic ataxia", Nat. Neurosci 3: 729-736, (2000); (b) spatial attention. See, Bisley J W & Goldberg M E "Neuronal activity in the lateral intraparietal area and spatial attention", Science 299:81-86, (2003a); Corbetta M & Shulman G L "Control of goal-directed and stimulus-driven attention in the brain," Nat Rev Neurosci 3:201-215, (2002); Laberge D, "Attentional Control: Brief and prolong". Psychol Res 66:230-233, (2002); Stein J, Glickstein M, "Role of the cerebellum in visual guidance of movement". Physiol Rev 72:972-10.17, (1992); and (c) eye movement. See, Andersen R A "Visual and eye movement functions of the posterior parietal cortexa". Ann Rev Neurosci 12:377-403, (1989); Bisley J W, Golberg M E, "The role of the parietal cortex in the neural processing of saccadic eye movements," Adv Neurol 93: 141-157, (2003b). Dyslexics perform worse in tasks which are thought to be mediated by the PPC. For example, dyslexics have problems with spatial attention focusing (orienting), smooth pursuit of targets, temporal planning of fixations (stable gaze) and saccadic eye movements (e.g. saccadic inhibition) and demonstrate symptoms similar to those suffering from unilateral neglect (e.g. LHF inattention vs. RHF enhance recognition).

Eye movements and attention are closely related. The shift of attention from one object to another is usually followed by a saccade, i.e., a fast jump of the gaze aiming to foveate the new object of interest. Both an attention shift and the subsequent saccade are parts of the orienting response. To illustrate the latter, Biscaldi et al. measured saccadic eye movements in a single target (re-fixation) and in a sequential-target task (target jumped from one position to another). See, Biscaldi M, Gezeck S, Stuhr V, "Poor saccadic control correlates with dyslexia," Neuropsychologia, 36:1189-1202, (1998). Their research indicated that, in relation to normal readers, dyslexics have much more scattered saccadic reaction times, i.e., many express saccades (i.e., saccades with latencies<135 misc.) and late saccades. They suggested that dyslexics' attentional shortcomings are responsible for their poorer saccadic control. In particular, they claimed that deficits in selective attention might result in deficits in fixation disengagements, and consequently in increased generation of late saccade and irregular saccade triggering.

The involvement of visual spatial attention in reading disorders has been clearly pointed out by Stein and Walsh. (See, Stein J, Walsh V, "To see but not to read; the magnocellular theory of dyslexia," Trends Neurosci 20:147-152, 1997). Visual spatial attention research in developmental dyslexia suggests that mastery of reading fluency may be delayed or impaired due to lack of automatic and effortless sight words' identification. The lack of automatic and effortless sight words' identification is manifested in anticipation of letters, frequent errors in reading word endings, misplacement of letters within a word, hesitated, interrupted and slow reading. Accordingly, Facoetti et al suggested that visual disorders, often associated with dyslexia, might be determined by a deficit of spatial attention, that is, a deficit of the mechanisms that inhibit lateral information distraction (attentional focus deficit). See, Facoetti A, Paganoni P, Lorusso M L, "The spatial distribution of visual attention in developmental dyslexia," Exp Brain Res 132:531-538, (2000a).

Still, additional studies centering on visual search tasks, have found that dyslexic children show poorer visual search performances in the left visual field (LVF) than in the right visual field (RVF), thus confirming asymmetric performances in dyslexic subjects. See, Eden G F, Stein J F, Wood F B, "Visuospatial ability and language processing in reading disabled and normal children," In: Wright S F, Groner R (ed) "Studies in visual information processing: facets of dyslexia and its remediation". North-Holland, Amsterdam, pp 321-335, (1993); Fowler M S, Richardson A J, Stein J F "Orthoptic investigation of neurological patients undergoing rehabilitation," Br Orthoptic J 48:2-27 (1991). Hari and Koivikko suggested that compared with the RVF, dyslexics suffer from "mini-neglect" in the LVF. See, Hari R, Koivikko H, "Left-side mini-neglect and attentional sluggishness in dyslexic adult," Soc Neurosci Abstr 25:1634, (1999). Based on Temporal Order Judgment (TOJ) research, showing a left-right asymmetry, Hari et al again hypothesized that dyslexics showed a LVF mini-neglect syndrome, a disadvantage of the left visual hemifield in selecting and processing visual information. See, Hari R, Renvall H, Tanskanen T "Left mini-neglect in dyslexic adults," Brain 124: 1373-1380, (2001). According to Hari et al, the mini-neglect syndrome is caused by magnocellular deficit. See, Hari R, Renvall H, Tanskanen T "Left minineglect in dyslexic adults," Brain 124: 1373-1380, (2001). Indeed, since the magnocellular system projects mostly to the parietal cortex, and the circuits controlling attention are located in the dorsal system, a diffuse functional disruption of the magnocellular pathway could weaken the input to this cortex. Moreover, the unilateral neglect syndrome usually stems from an impairment of the right, rather than the left, parietal cortex. Therefore, it seems reasonable to assume that generally weakened magnocellular input should result in a LVF disadvantage. This lateral spatial attention deficit in the LVF appears to be linked to a contralateral RVF enhancement in the processing of visual information, as demonstrated by an increased ability of dyslexics in letter recognition in the RVF. See, Geiger G, Lettvin J Y, Fahle M, "Dyslexic children learn a new strategy for reading: a controlled experiment," Vision Res 34:1223-1233 (1994). A strong inhibition in the LVF ("mini-neglect" in the left visual field) could also hamper rapid and exact planning of regression saccades (backward movements from right to left) that is fundamental for fluent and correct reading and which is known to be altered in children with dyslexia. See, Morris R K, Rayner K "Eye movements in skilled reading: implications for developmental dyslexia". In: Stein J F (ed) "Vision and visual dyslexia" MacMillan Press, London, 233-242 (1991).

Facoetti and Molteni also investigated the gradient of visual spatial attention in dyslexic children and in children with normal reading skills. Normally-reading children showed a normal symmetric distribution of spatial attention. In contrast, children with dyslexia showed an anomalous and asymmetric distribution of spatial attention. They hypothesized that a selective disorder of spatial attention is to blame for the spatial attention asymmetry (left inattention and right over-distractibility). See, Facoetti A, Molteni M, "The gradient of visual attention in developmental dyslexia," Neuropsychologia 39:352-357 (2001). Indeed, dyslexics exhibited a reduced interference effect in the LVF (mild left inattention), associated with a strong interference effect in the RVF (right over-distractibility) See, Facoetti A, Turatto M, "Asymmetrical visual fields distribution of attention in dyslexic children: a neuropsychological study," Neurosci Lett 290:216-218 (2000). An excessive inhibition of LVF stimuli (left inattention), associated with a lack of inhibition of RVF stimuli (right over-distractibility) may influence the automation skill necessary for effortless visuo-perceptual identification and decoding process of words, either by an anomalous suppression of identification of letters in the left side of a string, or by a difficulty in the inhibition of orienting visual attention (saccades) towards distracting visual peripheral stimuli coming from the RVF, which corresponds to the direction of reading of most languages.

Other evidence suggests that the magnocellular system, which plays a crucial role in the shifting of attention, is defective. See, Steinman B A, Steinman S B, Lehmkuhle S, "Transient visual attention is dominated by the magnocellular stream," Vision Res 36:589-599 (1996); Stein J, Walsh V, "To see but not to read; the magnocellular theory of dyslexia," Trends Neurosci 20:147-152 (1997). The Magnocellular system, which processes information about location and movement of visual stimuli, may affect reading by hampering the focus of attention (which requires precise coding of stimulus location). It has been shown that Magno cells dominate the dorsal-system projection from the primary visual cortex and further on to the parietal lobe's attentional and eye movement control regions. See, Livingstone M S, Hubei D H, "Segregation of form, color movement, and depth: anatomy, physiology and perception," Science 240:740-749 (1988). Therefore, an impaired dorsal-system flow of visual information reaching the Posterior Parietal Cortex (PPC) is suspected of compromising visual attention orienting in dyslexic children. See, Vidyasagar T R, "A neural model of attentional spotlight: parietal guiding the temporal," Brain Res Rev 30:66-76 (1999). Of relevance, Eden et al. found poor smooth pursuit, (smoothly tracking a slowly moving object in the visual field) in a dyslexic group, particularly when pursuing a target moving from left to right. Eden et al. proposed that eye-movement abnormalities might be due to the insufficient inhibition of Parvocellular activity from magnocellular activity. It should be also noted that left-right asymmetry reported by Eden et al. fits very well with the mini-neglect hypothesis. See, Eden G F, Stein J F, Wood M H, Wood F B, "Differences in eye movements and reading problems in dyslexic and normal children," Vision Res 34:1345-1358 (1994).

Still on the magnocellular system involvement in eye movements and visual spatial attention, there is also a direct contribution of dorsal transient circuits to visuo-motor activity, or as Goodale et al. put it, there are two different kinds of vision: vision-for-perception and vision-for-action. Vision-for-action is thought to extract the information which is necessary for immediate use from the dorsal visual stream in fast motor actions and to rely on computations made mainly in the dorsal system. See, Goodale M A, Westwood D A, Milner A D, "Two distinct modes of control for object-directed action," Prog Brain Res 144: 131-144 (2004).

Still on establishing a causal link between dyslexia and a deficit in the magnocellular system, there is strong research evidence suggesting that about two-thirds of dyslexic people have a low level deficit of the magnocellular visual system (Lovegrove, W., Martin, F., and Slaghuis, W. Atheoretical and experimental case for a visual deficit in specific reading disability, *Cognitive Neuropsychol*, 3, 225-67, 1986). Several studies have been conducted to compare the average performance of dyslexics to that of good readers. In general, these studies have found that: a) there is a reduced ability to detect flicker in dyslexic children, b) although there is a reduced ability to detect coarse detail, a normal ability was found to detect fine detail, c) there tends to be a prolonged persistence of the visual image, and d) dyslexic people have a decreased ability to detect fine motion. Additional studies discuss the higher perceptual outcomes level of magnocellular pathway impairment in dyslexic populations including perceptual grouping (Williams, M. C. and Bologna, N. B., Perceptual grouping in good and poor readers. *Perception and Psychophysics* 38, 367-375, 1985), (Solman, R. T., Cho, H., and Dain, S. J. Colour-mediated grouping effects in good and disabled readers, *Ophtal. Physiol. Opt.* 11, 320-7, 1991), sluggish foveal temporal processing, lack of inhibitory processes in peripheral visual processing spatial localization discrepancies Solman, R. T., May, J. G. Spatial localization discrepancies: a visual deficiency in poor readers, *Am. J. Psychol.* 103, 243-263, 1990), impaired visual temporal order judgment (May, J. G., Williams, M. C., Dunlap, W. P. Temporal order judgment in good and poor readers, *Neuropsychologia* 26, 917-24, 1988), improved visual search with target blurring, (Williams, M. C., May, J. G., Solman, R., Zhou, H. The effects of spatial filtering and contrast reduction on visual search times in good and poor readers, *Vision Res.*, 35, 285-91, 1995) and impaired visual search when distractors are present (Visyasagar, T., R. Pammer, K. Impaired visual search in dyslexia relates to the role of the magnocellular pathway in attention, *NeuroReport*, 10, 1283-7, 1999).

Accordingly, what is desired are systems and methods that promote eye-hand coordination.

BRIEF SUMMARY OF THE INVENTION

The present invention discloses, in a non-limiting embodiment, the novel implementation of a game-like task to promote eye-hand coordination via visuo-motor guided control of limb movements (e.g. the navigation of a graphical object [e.g. a car] by using a computer mouse to/and exerting repetitive right to left strokes' movements and vise a versa, trying to maintain the car as close as possible to a dividing line in the center of a road on a screen display.)

It is a feature of the present invention to provide a system that promotes effortless automatic sight word recognition of connected written text via delivery of non-verbal visual stimuli.

It is a further object of the invention to provide a system that promotes effortless automatic sight word recognition via delivery of novel non-verbal visual stimuli triggering visual spatial attention shifts in order to enhance fast recognition and processing of verbal and non-verbal target stimuli in either the left or right visual hemifield of a subject.

It is still further a feature of the invention to provide a system that promotes effortless automatic sight words recognition via delivery of novel non-verbal visual stimuli promoting inhibitory control of dorsal magnocellular transient neural networks, enabling accurate temporal planning of oculomotor movements, namely enabling proper transitions between stable gaze and eye saccades.

It is still further a feature of the invention to provide a system that promotes effortless automatic sight word recognition via delivery of novel non-verbal visual stimuli by the execution of a monotonous game-like task that consists in fast repetitive visuo-motor loops that strongly captivate the attentional focus of a subject in a manner that rapidly discriminates and processes salient features of a moving target(s), mainly in the fovea and parafoveal visual field. This motion-for-action novel visuo-motor activity greatly diminishes reorienting towards competitive distracting sensorial stimuli in the peripheral visual field, particularly for distracting sensorial stimuli in the RVF.

It is still a feature of the invention to provide a system that promotes effortless automatic sight words recognition of connected text via delivery of novel non-verbal visual stimuli targeting lexical processes underlying and contributing to reading fluency.

It is still further a feature of the invention to provide a system that promotes effortless automatic sight words' recognition via delivery of novel non-verbal visual stimuli for the execution of tasks where allocation of attentional resources will enable to focus in order to discriminate, process, retrieve and guide visuo-motor movement loops, while eliciting mild to low arousal in a subject.

It is yet further a feature of the invention to provide a system that promotes effortless automatic sight words recognition via delivery of novel non-verbal visual stimuli for the execution of tasks that will delay immediate self-gratification (e.g. score).

These and other features of the invention are accomplished in accordance with the principles of embodiments of the invention by systems and methods to promote in dyslexics and poor readers' an effortless automatic recognition of sight words by manipulating spatial attention when interacting with a monotonous game-like task. The herein teachings represent significant advances over the prior art.

We hypothesize that the teachings of the present invention represent a quantum leap in introducing novel ways of promoting plasticity in neural networks involved in reading. The present invention also teaches retraining of neural networks involved in reading via generation of novel non-verbal stimuli information that also triggers mild to low arousal in a subject. Such neural networks consist of (a) neural circuits involved in allocation and shifting of visual spatial attention; (b) transient neural dorsal circuits involved in timing and coordination of eye movements; and (c) perceptual-visuo-motor neural circuitry guiding eye-hand movements' loops. The multicomponent neural network that enables reading, although distributed across multiple areas in the brain, works in unison to promote, in a brief speck of time (about 280 milliseconds), automatic and effortless sight recognition of connected printed text, namely sight words recognition. Mastering an effortless and automatic recognition of sight words and their meaning enables reading fluency in dyslexics and poor readers, compensating in a relative short period of time for their disability and shortcomings in reading and enhancing their potential for integration in a modern literate society.

The present invention teaches an innovative but monotonous game-like task that promotes effortless automatic sight words recognition via delivery of novel non-verbal visual stimuli. The herein novel non-verbal visual stimuli also trigger visual spatial attention shifts in order to enhance fast recognition and processing of verbal and non-verbal target stimuli in either the left or right visual hemifield of a subject, preferably enhancing attentional focus at foveal and parafoveal targets (verbal and non-verbal stimuli) on the RVF of a subject mediated by the LH. The present invention teaches a game-like task that instigates neuroplasticity in a subject engaged in it which re-trains neural networks involved in promoting effortless automatic sight word recognition and brings about an inhibitory control upon oculomotor, visuo-motor movement loops and related selective executive cognitive behaviors mediated by the PFC. The present invention discloses a novel monotonous game-like task which consists in the generation of non-verbal stimuli and motor-perceptual-cognitive strategies directed towards sustaining a subject's physiological arousal in the mild to low levels; a main strategy disclosed in the present invention consists in not displaying any real-time feedback information about a subject's actual performance while he is engaged in the game-like task. A subject actuating the herein game-like task must forgo and/or postpone performance gratification. Accordingly, the present invention teaches that at such mild to low physiological arousal levels, a subject's alertness and attention will optimally promote effortless automatic sight word recognition via effective targeting of lexical processes, therefore improving a subject's reading fluency competency (higher arousal might result in the extreme opposite—attention deficit).

In an embodiment, in the first visuo-motor navigation stage, a subject navigates a first non-verbal stimuli (a graphical mobile object, a "yellow car" for example), maintaining it as long as possible and as close as possible to the dividing line in the center of a road in which it travels. A subject interacts with the game-like task via actuating fast repetitive linear movements along the horizontal "x" axis of a display, in left to right and right to left directions (repetitive eye-hand/fingers visuo-motor loops exercised in the same direction that our eyes and our hand move when reading or writing). According to an internal score attained during this mild to intensive navigation stage, a subject is presented with a number of difficulties comprising graphical objects or effects (e.g. rain, fog, etc.) that will challenge a subject ability to maintain the first non-verbal stimuli graphical planar mobile object close as possible to the dividing line in the center of a road in which it travels. This first navigation stage of mild to intensive visuo-motor activity lasts for 63 seconds.

In a second visuo-motor navigation stage, a subject experiences a gradual decrease of his/her visuo-motor activity by smoothly and slowly navigating a first graphical planar mobile object (e.g. car) and accurately maintaining it on a central dividing line in a road. This novel kind of navigation elicits ocular smooth tracking pursue upon the first non-verbal stimuli graphical mobile object this second navigation stage of decreased visuo-motor activity lasts for 21 seconds.

In a third stage, there is no interactive visuo-motor activity, only passive oculomotor tracking movements on a non-verbal planar object. A subject's eyes passively track generated novel planar non-verbal stimuli. The smooth tracking of novel generated planar non-verbal stimuli generates a further inhibitory effect upon a subject's oculomotor and selective neural networks in the PFC. The herein game-like task generates smooth tracking of novel generated planar non-verbal stimuli that has an instantaneous psycho-physiological effect that is immediately felt by a subject passively eye tracking the said display of novel planar non-verbal stimuli. Accordingly, the smooth tracking of novel generated planar non-verbal stimuli triggers a real-time autonomic parasympathetic response, namely inducing a further calming effect thus contributing to reducing/decreasing a subject's arousal condition to mild-low levels. This third passive eye tracking stage of oculomotor activity lasts variably between 14 to 63 seconds, in accordance with an embodiment of the present invention. Stages 1, 2 and 3 are recurrent in a loop of a minimal 4 times to a maximal 6 times, in accordance with an embodiment of the present invention.

The herein novel game-like task is displayed in a non-curvilinear surface display. More so, the game-like task is not displayed in "full screen"; rather, it is only displayed at the center portion of the screen (has surrounding limiting margins), in accordance with an embodiment of the present invention.

We describe the game-like task of the present invention to be "monotonous" since it does not trigger or induce: 1) Increase of aggressive thoughts, which in turn increase the likelihood that a mild or ambiguous provocation will be interpreted in a hostile fashion; 2) Increase of aggressive physical affect 3) Increase of general physiological arousal (e.g. a sustaining long term increase in heart rate, blood pressure, respiration, etc.) which tends to further promote the dominant emotional behavioral tendency physiologically supported by high sympathetic activity. 4) Direct imitation of recently observed aggressive behaviors. In summary, the absence of explicit real-time feedback about actual performance, elicits in a subject a perceptual-cognitive labeling about the novel nature of the novel game-like task being monotonous, boring and, to some degree, the subjective feeling about the overall experience of performing the game-like task as not being fun.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

EXEMPLARY DEFINITIONS

To aid the description of embodiments of the invention, this section provides definitions of terms used herein. These definitions are intended to provide an exemplary understanding of the embodiments disclosed herein, and are not necessarily limiting.

"Sight word" refers to any word that is recognized by a reader effortlessly and automatically. For the most part, sight words can't be taught through pictures and/or phonics instruction, since phonic analysis and decoding rules generally do not apply to sight words. Therefore, sight words cannot be "sounded out", and must be learned by sight. To learn sight words, a child will need to have them memorized. Some examples of sight words are: for, to, the, of, and, that, in, you, I, and she. Sight words are also words that have very high usage, particularly in the early stages of reading. Studies show that sight words make up 50-75 percent of all words used in school books, library books, newspapers, and magazines. The 25 most common sight words make up about one-third of all written material. Without any doubt, sight words play an important role in a child's early education and his reading abilities' acquisition. Mastering automatic and effortless sight words recognition will ultimately help a child develop into a smooth and proficient reader.

"Non-verbal stimuli" refers to visual cues which have non-orthographic representations. Orthographic representations are single letters and/or the alphabetic code of any language and/or a string of connected letters representing words, pseudo-words, or non-words. Examples of non-verbal stimuli include visual cues which depict non-orthographic visual representations such as geometrical shapes and/or colors and/or numbers, their possible spatial-temporal-kinematical states and/or combinations and/or arrangements.

"Oculomotor" refers to, generally speaking, how the brain controls the muscles that focus and move the eyes. In particular, the oculomotor nerve is the third of twelve paired cranial nerves. It controls most of the eye's movement, constriction of the pupil, and maintains an open eyelid. Cranial nerves IV and VI also participate in control of eye movement.

"Visuo-motor" refers denoting the ability to synchronize in the cerebral cortex visual information with physical movement or pertaining to those motor activities that are dependent on visual coordination. Cortical visual information processing in the brain is transformed for different purposes in different ways. Visuo-motor herein denotes vision for action being the visual control of skilled actions in relation to targets. Vision for action is served by the dorsal stream. The dorsal stream guides action by registering visual information about the target in a moment-to moment basis. This bottom-up visual information reaching from the retina is transformed to specify the required movement parameters, such as the kinematical path for reaching and the required grip aperture for grasping the target. See, Goodale M A, Milner A D "Separate visual pathways for perception and action" Trends in Neuroscience, 15, 20-25, (1992); Goodale M A, Milner A D, "Sight unseen: An exploration of conscious and unconscious vision" Oxford University Press, Oxford-New York, (2004); Milner A D, Goodale M A "Visual pathways to perception and action" In T P Hicks, S. Molotchnikoff & T. Ono (Eds.) Progress in Brain Research, 95: 317-337, (1993), Amsterdam: Elsevier; Milner A D, Goodale M A "The Visual Brain in Action", Oxford University Press, Oxford, (1995); and Milner A D, Goodale M A "The Visual Brain in Action" Second Edition. Oxford: Oxford University Press, (2006).

"Eye (ocular) fixation" refers to the maintenance of the visual gaze (the fovea) on a single fixed location. Eye fixation refers to directing the gaze (positioning and accommodation of the eyes) in such a manner that the visual image of the object falls on the fovea centralis of the retina, the area where vision is the most acute. The human body typically alternates saccades and visual fixations. Fixational eye movement occurs involuntarily, and visual fixation is never perfectly steady. Reading involves fixating on successive locations across the page or screen. The average fixation time duration in reading is in the order of 200 to 250 msec. Readers acquire information from text only during fixations. See, Wolverton G S, Zola D A "The temporal characteristics of visual information extraction during reading" in K. Rayner (Ed.), Eye movements in reading: Perceptual and language processes, 41-51, (1983), New York: Academic.

"Eye saccades" refers to a fast movement of the eye, a rapid, small, abrupt eye movement, as that which occurs when the eyes fix on one point after another in the visual field. In human eyes, large saccades reach peak velocities of up to 800°/s. Saccades serve to bring the retinal image of an object of interest to be situated on the fovea. Saccades are initiated by eye fields in the frontal and parietal lobes of the brain and are the fastest movements produced by the human body; once underway they cannot be altered by will. Eye saccades serve as a mechanism for fixation, typically very accurate, bringing the eyes to within a fraction of a degree of the desired position. Saccades to an unexpected stimulus normally require about 200 msc to initiate, and then last from about 20-200 msc, depending on their amplitude (20-30 msc is typical in language reading). In addition to the saccadic motion, the eyes vibrate at a rate of about 30 to 70 hertz. These vibrations cause the eye to refresh the image to the brain. The vibrations are named microsaccades. Of most importance is the fact that the brain cannot retain an image if our eyes fixate on it without moving. The function of the eye-brain connection is complex and requires perpetual movements to continually make impressions on the brain. Eye saccades also serve as a mechanism to generate rapid eye movement and the fast phase of optokinetic nystagmus.

"Visual attention" refers to what we see at any given instance, which is determined by what we attend to in the environment. Because the human brain is limited in its ability to process information, shifting of visual attention is necessary as it allows us to redirect attention to aspects of the environment which are more relevant to us. At any given time, the environment presents far more perceptual information than can be effectively processed. Visual attention is a selective information mechanism shows us to bring to focus information that is most relevant to our ongoing behavior. First, visual attention can be used to select behaviorally relevant information and/or to ignore the irrelevant or interfering information. Second, attention can modulate or enhance this selected information according to the state and goals of the perceiver.

"Visual attentional shifts/orienting" refers to the idea of attention being like a movable spotlight (moving-spotlight theory) that is directed towards intended targets in the environment, focusing on each target in a serial manner. When information is illuminated by the spotlight, hence attended, processing proceeds in a more efficient manner. However, when a shift of spatial attention occurs, the spotlight is, in effect, turned off while attention shifts to the next attended location. See, Sperling G, Weichselgartner E "Episodic theory of the dynamics of spatial attention" Psychological Review, 102, 503-532 (1995); LaBerge D, Carlson R L, Williams J K, Bunney B G "Shifting Attention in Visual Space: Tests of Moving-Spotlight Models Versus an Activity-Distribution Model". Journal of Experimental Psychology: Human Perception and Performance 23(5):1380-1392, (1997). In the 1990s, Posner and Petersen proposed to break attentional shifts into three distinct stages of visual attention orienting. (See, Eysenck M W, Keane M T "Cognitive Psychology: A Student's Handbook" (5th ed.) New York, N.Y.: Psychology Press, 2005). The first stage relates to visual attention disengagement from where it is currently focusing. The second stage relates to the physical act of shifting of one's visual attention from one spatial location to another. The third stage relates to how visual attention would be engaged onto the new spatial location. Visual spatial attention changes can take place with the eyes moving, overtly, or with the eyes remaining fixated, covertly. See, Wright R D, Ward L M "Orienting of attention" Oxford University Press, (2008). Prior to an overt eye movement, where the eyes move to a target location, covert attention shifts to this location. See, Hoffman J, Subramaniam B, "The role of visual attention in saccadic eye movements", Perception & Psychophysics, 57 (6), 787-795, (1995); Kowler E, Anderson E, Dosher B, and Blaser E. "The role of attention in the programming of saccades" Vision Research 35:1897-1916, (1995); Deubel H, Schneider W "Saccade target selection and object recognition: evidence for a common attentional mechanism" Vision Research 36: 1827-1837, (1996); Peterson M S, Kramer A F, Irwin D E "Covert shifts of attention precede involuntary eye movements" Perception & Psychophysics, 66, 398-405, (2004). Nevertheless, it is equally important to understand that visual attention can also shift covertly to objects, locations or even to mentation processes (thoughts) while the eyes remained fixated on some spatial target. Utilizing functional magnetic resonance imaging (fMRI) has illuminated our understanding of mechanisms that drive visual attention to different spatial locations and demonstrated that the superior parietal cortex may play an important role in shifting attention around spatial locations in space. This would be particularly important for visual search tasks which require attention to move from one object to the other. In conclusion, many neural mechanisms are involved in shifts of visual attention and much of the research points in the direction of common neural network See, Corbetta M, Miezin F M, Shulman G L, & Petersen S E "A PET study of visuospatial attention" Journal of Neuroscience, 13, 1202-1226, (1993); Nobre A C, Sebestyen G N, Gitelman D R, Mesulam M M, Frackowiak R S, & Frith, C D "Functional localization of the system for visuospatial attention using positron emission tomography" Brain, 120 (Pt 3), 515-533, (1997); Corbetta M, Akbudak E, Conturo T E, Snyder A Z, Ollinger J M, Drury H A, Linenweber M R, Petersen S E, Raichle M E, Van Essen D C, Shulman G L "A common network of functional areas for attention and eye movements" Neuron 21:761-773, (1998).

"Visual field" refers to what we can see without moving our heads or eyes. Each eye sees only a portion of this visual field. The visual field of each eye can be divided into right and left visual hemifields. Through the optic chiasm to the visual cortex, the visual signals from the left hemifields of both eyes are sent to the right hemisphere of the brain (the left visual hemifield is seen by the nasal left retina and temporal right retina) while the signals from the right hemifields of both eyes are sent to the left hemisphere of the brain (the right visual hemifield is seen by the temporal left retina and nasal right retina), so each hemisphere of the brain is responsible for processing the visual information in the opposite visual field from both eyes.

"Dyslexia" refers to a broad term defining a learning disability that impairs a person's reading fluency or comprehension and which can manifest itself as a difficulty in phonological awareness, phonological decoding, orthographic coding, auditory short-term memory, or rapid naming. Dyslexia is the most common specific learning difficulty (SpLD) particularly in regards to literacy (reading and spelling). It affects about 5-10% of the population, persists throughout life and runs in families. Most people with dyslexia do not have overt difficulties with spoken language, yet have marked difficulties with written language. In dyslexic people, reading and/or spelling are markedly below the level expected on the basis of age and intelligence. Early common symptoms of dyslexia among preschool children are: slow learning of new words, difficulty in rhyming words, and low letter familiarity; common symptoms of dyslexia among young primary school students are: difficulty learning the alphabet or letter order, difficulty with associating sounds with the letters that represent them (sound-symbol correspondence), difficulty identifying or generating rhyming words, or counting syllables in words (Facoetti, A., Corradi, N., Ruffino, M., Gori, S. and Zorzi, M., Visual Spatial Attention and Speech Segmentation are both Impaired in Preschoolers at Familial Risk for Developmental Dyslexia, *Dyslexia,* 16:226-239, 2010) (phonological awareness), difficulty segmenting words into individual sounds, or blending sounds to make words (phonemic awareness), difficulty learning to decode written words and difficulty with word retrieval or naming problems (Jones, M. W., Branigan, H. P and Kelly, M. L., Dyslexia and non-dyslexic reading fluency: Rapid automatized naming and the importance of continuous lists, *Psychonomic Bulletin & Review,* 16(3), 567-572, 2009); common symptoms of dyslexia among older primary school students are: slow or inaccurate reading, very poor spelling, difficulty reading out loud, reading words in the wrong order, skipping words and sometimes guessing words, difficulty associating individual words with their correct meanings, difficulty with time keeping and concept of time when doing a certain task, and difficulty with organization skills. Neuroimaging studies using (fMRI) and (PET) have found clear evidence for structural and functional differences in children with reading difficulties. It has been found that people with dyslexia have a deficit in parts of the left hemisphere of the brain that is associated with the process of reading, which includes the inferior frontal gyrus, inferior parietal lobule, and middle and ventral temporal cortex (Cao, F, Bitan, T, Chou T, Burman D. D. and Booth J. R., Deficient orthographic and phonological representations in children with dyslexia revealed by brain activation patterns, *J Child Psychol Psychiatry,* 47 (10): 1041-1050, 2006). A study in the University of Maastricht revealed that adult dyslexic readers underactivate the superior temporal cortex for the integration of letters and speech sounds (Blau V. Atteveldt, N., Ekkebus, M, Goebel R., Blomert L., Reduced Neural Integration of Letters and Speech Sounds Links Phonological and Reading Deficits in Adult Dyslexia, *Current Biology,* 19, 503-508, 2009). Scientists also claim that clues to a neurological cause of dyslexia may lie in the region of the corpus callosum, a thick bridge of neural tissue in the middle of the brain connecting the two hemispheres, conveying information from one side to the other.

"Posterior parietal cortex" refers to Broadmann's area 5, 7a and 7b. Area 5 receives information from somatosensory areas 1, 2, and 3 of the cortex. Area 7 further integrates the already highly integrated signals from the visual areas of the cortex, such as MT and V5. These fields were recognized on cytoarchitectural criteria. Further neuroanatomical, clinical and physiological investigations revealed that cells in PPC form small (ca. 0.25 $cm^2$) subregions of different connectivity and response properties See, Andersen R A & Buneo C A "Sensorimotor integration in posterior parietal cortex" Adv Neurol 93: 159-177, (2003). Traditionally the posterior parietal cortex was believed to be an "association area", a higher-level sensory structure responsible for associating different sensory modalities. Indeed, in both human and non-human primates is known to play a crucial role in the early integration of visual information with somatosensory, proprioceptive and vestibular signals. The PPC plays an important role in producing planned movements. The parietal cortex receives somatosensory, proprioceptive, and visual inputs (magnocellular dorsal stream), and then uses them to determine such things as the positions of the body and the target in space. It thereby produces internal models of the movement to be made, prior to the involvement of the premotor and motor cortices. The parietal lobes are themselves closely interconnected with the prefrontal areas, and together these two regions represent the highest level of integration in the motor control hierarchy. Much of the output of the posterior parietal cortex goes to areas of frontal motor cortex: the dorsolateral prefrontal cortex, various areas of the secondary motor cortex, and the frontal eye field. fMRI studies in monkeys and Transcranial Magnetic Stimulation (TMS) studies in humans indicate that the PPC comprises a medley of small areas, each specialized for guiding particular movements of eyes, head, arms or hands. Additionally, a number of neuropsychological studies confirmed the hypothesis that the brain structures controlling attention are situated in PPC. See, Posner M I & Cohen Y "Components of visual orienting of attention" J Neurosci 4: 1863-1874, (1984). Two mechanisms of attention are PPC relevant. See, Corbetta M, Shulman G L "Control of goal-directed and stimulus-driven attention in the brain," Nat Rev Neurosci 3:201-215, (2002). The first, the stimulus-driven attention mechanism operates in bottom-up fashion and its role is to capture an intrinsic property of the stimulus, provided that it is sufficiently salient to divert attention from the current focus. Therefore, it enables the processing of novel, unexpected events. It has been shown that the tasks engaging the stimulus-driven attention activate the temporo-parietal junction (TPJ). See, Downar J, Crawley A P, Mikulis D J, Davis K D "The effect of task relevance on the cortical response to changes in visual and auditory stimuli: An event-related fMRI study" Neuroimage 14: 1256-1267, (2001). The second, goal-driven, attention mechanism operates in top-down fashion, is involved in the voluntary control of attention (superior parietal lobule (SPL) and precuncus (PC) and consists in shifting or focusing attention according to one's will. See, Giesbrecht B, Woldorff M G, Song A W, Mangun G R "Neural mechanisms of top-down control during spatial and feature attention" Neuroimage 19: 496-512, (2003); Yantis S, Schwarzbach J, Serences J T, Carlson R L, Steinmetz M A, Pekar J J, Courtney S M "Transient neural activity in human parietal cortex during spatial attention shifts", Nat Neurosci 5: 995-1002, (2002). Also important to PPC are parietal regions controlling eye movements. The so-called parietal eye field (PEF) is located in the intraparietal sulcus. Two other nearby structures involved in eye-movement control are located in TPJ, at the border between the temporal and parietal lobes. These are the middle temporal area (area MT) and the medial superior temporal area (MST). See, Pierrot-Deseilligny C, Gaymard B, Müri R, Rivaud S "Cerebral ocular motor signs", J Neurol 244: 65-70, (1997). Lesion of PEF leads to elongation of the latency and reduction of accuracy of reflexive saccades (i.e., saccades which are triggered by a visual target suddenly appearing in the visual field). See, Pierrot-Deseilligny C, Rivaud S, Gaymard B, Agid Y, "Cortical control of reflexive visually guided saccades in man", Brain 114: 1473-1485, (1991a); Pierrot-Deseillingny C, Rivaud S, Gaymard B, Agid Y, "Cortical control of memory-guided saccades". Ann Neurol 37: 557-567, (1991b). Damage to the PPC can produce a variety of sensorimotor deficits, including deficits in the perception and memory of spatial relationships, in accurate reaching and grasping, in the control of eye movement, and Inattention. The two most striking consequences of PPC damage are apraxia (a disorder with motor planning) and hemi spatial neglect. For example, a stroke affecting the right parietal lobe of the brain can lead to neglect for the left side of the visual field, causing a patient with neglect to behave as if the left side of the sensory space is nonexistent. Parietal deficits have also been proposed as a cause of developmental dyslexia. Dyslexics were shown to perform worse on tasks which are thought to be mediated by the posterior parietal cortex. For example, they have problems with attention focusing, pursuit and saccadic eye movements and show some symptoms similar to those shown by people suffering from unilateral neglect. In summary, the posterior parietal cortex, which receives most of its input from the magnocellular system (See (1) Steinman, S. B., Steinman, B. A., Vision and attention. 1: Current models of visual attention, *Optom, Vis. Sci.* 75, 146-55, 1998; (2) Steinman, S. B., Steinman, B. A., Trick G. L., Lehmkuhle, A sensory explanation for visual attention deficits in the elderly, *Omtom. Vis. Sci.*, 71, 743-9, 1994), plays a critical role in the influence of visual attention on saccadic, pursuit, and vergence eye movements (Colby, C. L., The neuroanatomy and neurophysiology of attention. *J. Child Neurol.* (suppl) 6, S88-S116, 1991; and Stein, J. F. Review article: Representation of egocentric space in the posterior parietal cortex. Quart. *J. Exp. Physiol.* 74, 583-606, 1989)). Researches have hypothesize that visual attention deficits might cause ocular motor dysfunction in dyslexics. Prior a saccadic or pursuit eye movement takes place, visual attention needs to be oriented to the target position (Hoffman, J. E., Subramaniam, B. The role of visual attention in saccadic eye movements, *Percept. Psychophys.*, 57, 787-95, 1995), and shifts in visual attention be an important mechanism in enabling vergence eye movements (Shelhamer, M., Merfeld, D. M., Mendoza, J. C. Vergence can be controlled by audio feedback, and induces downward ocular deviation. *Exp. Brain Research,* 101, 169-172, 1994).

"Visual Magnocellular system" refers to a 10% of ganglion cells also named M cells, which axons provide visual signals that travel from the eye to the rest of the brain and which are noticeable larger (magno-larger in Latin) than the remainder smaller (parvo-smaller in Latin) ganglion cells. See, Enroth-Kugel C and Robson J G "The contrast sensitivity of retinal ganglion cells in the cat" Journal of Physiology, 187, 517-552, (1966); Shapley R and Perry V H "Cat and monkey retinal ganglion cells and their functional roles". Trends in Neuroscience, 9, 229-235, (1986). M cells are primarily concerned with visual perception. Particularly, these cells are responsible for resolving motion and coarse outlines. The magno cells have larger receptive fields thus gather light from a larger area and consequently they are more sensitive to fast transient changes in light (flickering) and fast-conducting over a larger area, but not receptive to objects' fine detail or color. See, Maunsell J H R, Nealey T A and DePriest D D "Magnocellular and parvocellular contributions to responses in the Middle Temporal Visual Area (MT) of the macaque monkey". Journal of Neuroscience, 10 (10), 3323-3334, (1990); Merigan W H and Maunsell J R "How parallel are the primate visual pathways?" Annual Reviews in Neuroscience, 16, 369-402, (1993). M cells project to the primary visual occipital cortex via two ventral magnocellular layers in the main relay nucleus, the lateral geniculate nucleus (LGN). As visual information leaves the occipital lobe, it is processed in the brain in two distinct pathways, a dorsal stream and a ventral stream. See, Mishkin M, Ungerleider L G, "Contribution of striate inputs to the visuospatial functions of parieto-preoccipital cortex in monkeys." Behay. Brain Res. 6 (1): 57-77, (1982). The dorsal stream commences with purely visual functions in the occipital lobe before gradually transferring to visual spatial awareness at its termination in the parietal lobe. The dorsal stream, commonly referred to as the "where" stream, is involved in spatial attention (covert and overt), and communicates with regions that control eye movements and hand movements. More recently, this area has also been called the "how" stream to emphasize its role in perception for action-guiding behaviors to spatial locations. Despite the intermingling of magno and parvo inputs in the primary visual cortex, the dorsal stream is dominated by input form the visual magnocellular system. Therefore, the dorsal stream plays a decisive role in visual processes guiding eye and limb movements, and it projects onwards to the frontal eye fields, subcortical visual structures, such as the superior colliculus (via the thalamus) and cerebellum, which are all very important for guiding and controlling visuo-motor behavior. The visual magnocellular system contributes extensively to reading. The visual magnocellular system is responsible for timing visual events when reading. Thus, sensitivity to visual motion seems to help determine development of orthographic skill in both proficient and reluctant readers. In general, good magnocellular function is vital for high motion sensitivity and stable binocular fixation, hence essential for proper development of orthographic skills.

"Inhibitory control of cognitive/motor behavior" refers to inhibitory control, which includes the ability to refrain from automatically reacting to external events, the ability to prevent internal impulses, or the ability to simply cancel an already planned action. The ability to suppress irrelevant information and action becomes more efficient with age. Cognitive inhibitory processes and their control begin very early in life and mature steadily throughout childhood development. Scientific literature about developmental studies has clearly demonstrated that cognitive abilities develop throughout childhood. See, Case R, "Validation of a neo-Piagetian capacity construct" Journal of Experimental Child Psychology, 14, 287-302 (1972); Diamond A & Doar B, "The performance of human infants on a measure of frontal cortex function, the delayed response task", Developmental Psychobiology, 22, 271-294 (1989). More so, immature cognition is characterized by susceptibility to interference in overriding an attentional or behavioral response. See, Brainerd C J & Reyna V F, "Memory independence and memory interference in cognitive development", Psychological Review, 100, 42-67 (1993); Munakata Y, "Infant preservation and implications for object permanence theories: a PDP model of the AB task," Developmental Science, 1, 161-184 (1998). Classically, response inhibition has been considered to arise essentially from bottom-up reactive processes (triggered by NoGo or Stop signals for example). Typical brain regions involved in response inhibition are the bilateral ventral prefrontal cortex, the right parietal lobe and the right dorsolateral prefrontal cortex.

"Arousal" refers to a state of responsiveness to sensory stimulation or excitability, a condition of sensory alertness, mobility and readiness to respond. Arousal is a physiological and psychological state of being alert, physically and mentally. It involves the stimulation of the reticular activating system in the brain stem, in the autonomic nervous system and in the endocrine system. Leading signs of arousal are increased heart rate, increased blood pressure and fast and shallow respiration. Physiological arousal levels are mediated by the antagonistic interaction of the sympathetic-parasympathetic nervous systems; maturation of the parasympathetic system is accompanied by increase in the capacity to inhibit sympathetic activity resulting in a reduction in mobilization and baseline levels of arousal.

"Delay/deferred gratification" refers to the ability to forgo an immediate pleasure or reward in order to gain a more substantial one later on. To function effectively, individuals must voluntarily postpone immediate gratification and persist in goal-directed behavior for the sake of future outcomes. In the late 1960s and early 1970s, Mischel pioneered landmark studies with preschoolers, shedding light on the ability to delay gratification and to exert self-control in the face of strong situational pressures and emotionally temptations. See, Mischel W, "Theory and research on the antecedents of self-imposed delay of reward", In B. A. Maher (Ed.), Progress in experimental personality research, 3:85-132, (1966). San Diego, Calif.: Academic Press; Mischel W, Ebbesen E B & Zeiss A R "Cognitive and attentional mechanisms in delay of gratification", Journal of Personality and Social Psychology, 21, 204-218, (1972). These studies examined the processes and mental mechanisms that enable a young child to forego immediate gratification and to wait for a larger desired but delayed reward instead. These studies suggested that long-term prediction may be possible. When these children became adolescents, their parents rated them as more academically and socially competent, verbally fluent, rational, attentive, planful, and able to deal well with frustration and stress. See, Mischel W, Shoda Y & Peake P K "The nature of adolescent competencies predicted by preschool delay of gratification", Journal of Personality and Social Psychology, 54, 687-696, (1988). Delay of gratification is a cognitive inhibitory ability depicting self-control that steadily matures (improves) from early childhood into adolescence. Individuals often do not internalize delay of gratification until the teen years or later.

"Associative learning" refers to a learning process in which discrete ideas and percepts which are experienced together become linked to one another. It is a learning process also referred to as 'classical conditioning'.

"Reading Fluency" refers to the ability to read phrases and sentences smoothly and quickly, while understanding them as expressions of complete ideas. Cognitive capacity that builds up as a result of mastering an automatic word decoding, frees attentional resources that fluent readers can use for expressive comprehension of the text. Reading fluency is a multidimensional ability that can be summarized into the following three components: 1) Accuracy, or accurate decoding of words in text; 2) Quick, automatic and effortless recognition of words in a connected text, with minimal use of attentional resources; and 3) Prosody, or the appropriate use of phrasing and expression to convey meaning in the interpretation of text. Reading fluency can be conceptualized as establishing a direct link between the two major components of reading—word decoding and comprehension. At one end of this link, reading fluency connects to accuracy and automaticity in decoding. At the other end of this link, reading fluency connects to comprehension through prosody or expressive interpretation.

"Lexical item" refers to a single word or chain of words that forms the basic elements of a language's lexicon (vocabulary).

"Lexical route" As we read, our brain processes the written word simultaneously on two mental routes to interpret meaning, known as the lexical and the phonological. The "lexical route" relies on (automatic) activation of word-specific orthographic and phonological memory. The lexical route mechanism associates the visual word as a whole entity with its meaning and pronunciation; namely it identifies an orthographic representation (i.e. letters and their sequences and groups) in the orthographic lexicon, and articulates a phonological output lexicon (sounds). The lexical route can process all familiar words, regardless of whether they are regular or irregular in terms of their letter-sound relationships, but it fails processing unfamiliar words or non-words because they lack lexical representations.

"Temporal order judgment" (TOJ) refers to a psychophysical task where participants decide which one of two (or more) unimodal cues (e.g. audio or video) was presented first in a cross-modal stimulus. Alternatively, unimodal (auditory, visual or tactile) TOJ generally involves deciding in which of two spatial locations the stimulus was presented first. A number of experimental studies have provided evidence that the minimal required inter-stimulus-interval (ISI) between two successive stimuli, for correctly reporting their temporal order is about 20-40 msc. See, Hirsh I J & Sherrick C E Jr. "Perceived order in different sense modalities", Journal of Experimental Psychology, 62, 423-432 (1961); Pöppel E "A hierarchical model of temporal perception", Trends Cogn Sci 1: 56-61 (1997). This temporal order threshold appears to be remarkably invariant for auditory, visual, tactile and two-modality stimuli in normal subjects. See, Hirsh I J & Sherrick C E Jr. "Perceived order in different sense modalities". Journal of Experimental Psychology, 62, 423-432 (1961); Swisher L, Hirsh I J "Brain damage and the ordering of two temporally successive stimuli", Neuropsychologia 10: 137-152 (1972). Such a perceptual phenomenon is probably due to a central mechanism responsible for temporal ordering, which is independent of the sensory stimulus itself, the temporal cortex of the left hemisphere most likely responsible for TOJ. See, Efron R "The effect of handedness on the perception of simultaneity and temporal order", Brain, 86, 261-284 (1963); Tallal P, Merzenich M M, Miller S, Jenkins W "Language learning impairments: integrating basic science, technology, and remediation", Exp. Brain Res. 123: 210-219 (1998); Von Steinbüchel N, Wittmann M, Szelag E "Temporal constraints of perceiving, generating, and integrating information: Clinical indications", Restor. Neurol. Neurosci. 14: 167-182 (1999a).

"Graphical reference marker" refers to a graphical marker depicting a point, line or an area in a graphic object of the herein invention.

This section provides definitions of terms used herein. Such definitions are provided in this section for the convenience of the reader, although it is noted that these terms are further described in other sections contained herein. Variations and/or extensions of the following definitions applicable to the present invention will be apparent to persons skilled in the relevant art(s) based at least on the teachings contained herein. In continuation, the definitions are discussed in the context of the present invention, such that the theoretical overview of the invention is continued in this section.

BRIEF DESCRIPTION OF THE DRAWINGS/FIGURES

The accompanying drawings, which are incorporated herein and form a part of the specification, illustrate embodiments of the present invention and, together with the description, further serve to explain the principles of the invention and to enable a person skilled in the relevant art to make and use the invention.

FIG. 3 is a block diagram of Parameters Configuration Module Table, in accordance with an embodiment of the present invention.

FIG. 4 is a block diagram of Module Challenge Parameter, in accordance with an embodiment of the present invention.

FIG. 7 is a schematic description of Eye tracking task line trajectories, in accordance with an embodiment of the present invention.

Figure 1:
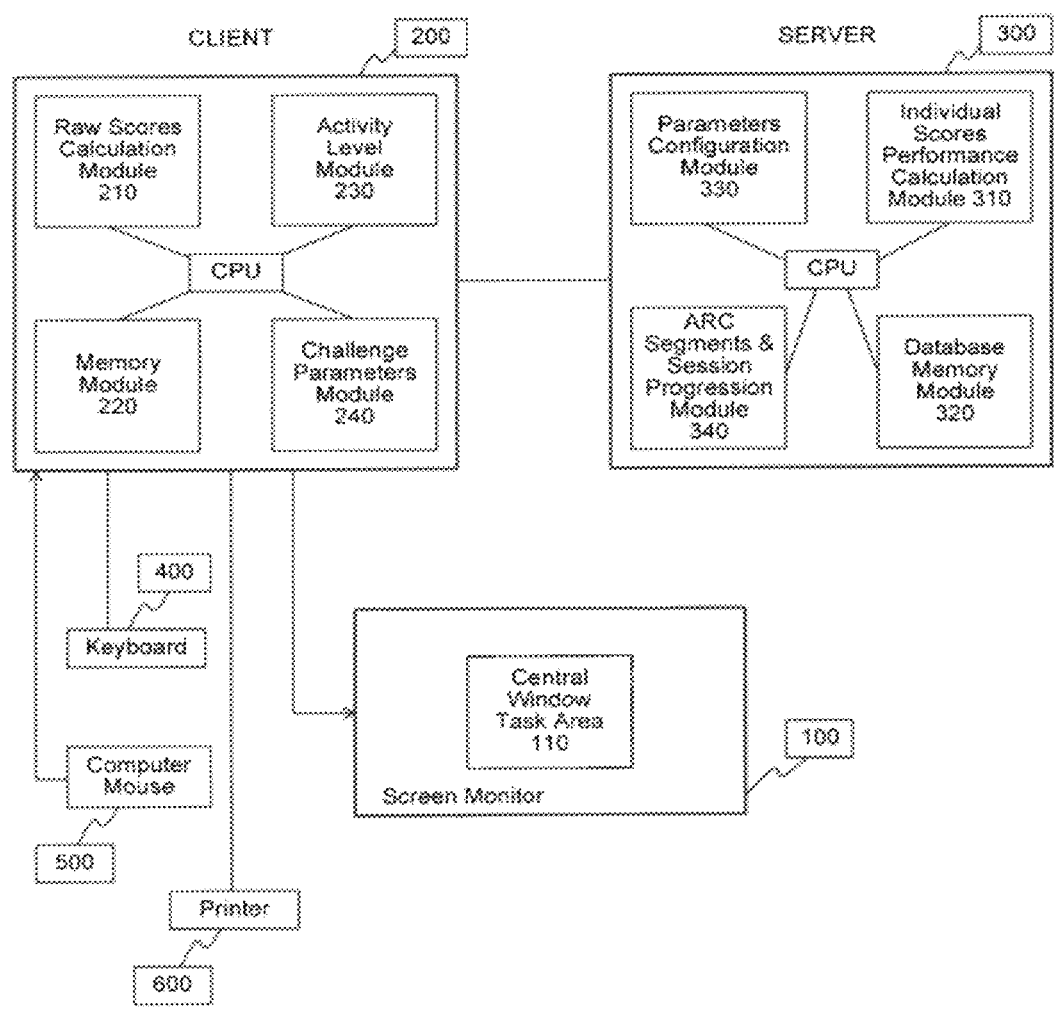
FIG. 1 is a block diagram overview of a system to generate non-verbal stimuli to promote visuo-motor movement loops and oculomotor movements in a game like-task according to an embodiment of the present invention.

The present invention will now be described with reference to the accompanying drawings. In the drawings, generally, like reference numbers indicate identical or functionally similar elements. Additionally, generally, the left-most digit(s) of a reference number identifies the drawing in which the reference number first appears.

DETAILED DESCRIPTION OF THE INVENTION

I. Introduction

The following detailed description of the present invention refers to the accompanying drawings that illustrate exemplary embodiments consistent with this invention. Other embodiments are possible, and modifications can be made to the embodiments within the spirit and scope of the invention. Therefore, the detailed description is not meant to limit the invention. Rather, the scope of the invention is defined by the appended claims.

It would be apparent to one of skill in the art that the present invention, as described below, can be implemented in many different embodiments of software, hardware, firmware, and/or the entities illustrated in the figures. Any actual software code with the specialized control of hardware to implement the present invention is not limiting of the present invention. Thus, the operational behavior of the present invention will be described with the understanding that modifications and variations of the embodiments are possible, and within the scope and spirit of the present invention.

Reference to modules in this specification and the claims means any combination of hardware or software components for performing the indicated function. A module need not be a rigidly defined entity, such that several modules may overlap hardware and software components in functionality. For example, a software module may refer to a single line of code within a procedure, the procedure itself being a separate software module. One skilled in the relevant arts will understand that the functionality of modules may be defined in accordance with a number of stylistic or performance-optimizing techniques, for example.

The present invention relates to system, method and computer program product embodiments to promote effortless automatic recognition of sight words via generation of novel non-verbal stimuli that manipulate dyslexics' and poor readers' visual spatial attention. By use of novel non-verbal stimuli, the herein invention enhances visual discrimination and accelerates processing of sight words, eliciting visual spatial attentional shifts, while also increasing inhibitory control upon oculomotor and visuo-motor activities and upon selective cognitive executive functions mediated by the prefrontal cortex. This is achieved by effectively orienting, shifting and focusing a subject's attentional resources during his/her sensorial reaction to novel non-verbal visual stimuli while performing a monotonous game-like task. The present invention has applications to a wide range of non-verbal pre-orthographic visual processes; the aim of such applications is to promote effortless automatic recognition of sight words. The present invention stimulates lexical processes, not only contributing to reading fluency of dyslexics, reluctant and slow readers, but also of beginning readers. The present invention promotes effortless automatic sight words recognition via generation of novel non-verbal stimuli addressing a subject's deficits which stem from flawed visual spatial attentional processes and from lack of optimal inhibitory control of oculomotor and visuo-motor loop movements and related selective executive functions mediated by the Pre-Frontal Cortex (PFC). The present invention teaches an innovative game-like task that generates a novel non-verbal stimuli which engages a shared neural network on both brain hemispheres to effectively ameliorate skills necessary for an effortless and automatic proficiency of the written word.

There is solid research that demonstrates strong likelihood that an impaired attentional system causes reading problems. Therefore, the findings of attentional problems in dyslexics could provide a plausible link between their magnocellular deficits and their reading problems. Omtzigt et al. directly addresses the causation link between magnocellular deficits and reading problems. In his experiment, subjects had to name a letter flanked by two other letters. When the letters were written with a magno-disadvantageous color contrast, naming accuracy was significantly lower than when the letters were written in parvo-disadvantageous weak luminance contrast. Omtzigt claimed that this finding supports the contribution of the magnocellular system to the allocation of attention and thus focuses on the importance of attention in reading difficulties. See, Omtzigt D, Hendriks A W, Kolk H H, "Evidence for magnocellular involvement in the identification of flanked letters," Neuropsychologia 40: 1881-1890 (2002).

The end goal in learning to read is to attain comprehension of the text. The first step we take to reach this goal is to master reading fluency. Felton defined fluency as "the ability to read connected text rapidly, smoothly, effortlessly, and automatically with little conscious attention to the mechanics of reading, such as decoding". See, Meyer M S & Felton R H, "Repeated reading to enhance fluency: Old approaches and new directions," Annals of Dyslexia, 49, 283-306 (1999). A first benchmark for fluency is being able to "sight read" some words. Meaning, reading fluency focuses on quick and automatic visual recognition of words in a connected text. The idea is that children will spot the most common words in their native language, and that the automatic recognition of these common important words will allow them to read and understand text faster.

Ehri chooses automatic effortless words' sight recognition as the fundamental skill necessary to master proficiency in reading "the ability to read words by sight automatically is the key to skilled reading". See, Ehri, L C "Grapheme-phoneme knowledge is essential for learning to read words in English" In J. L. Metsala & E. C. Ehri (Eds.), "Word recognition in beginning literacy" pp. 3-40 (1998). Mahwah, N J: Erlbaum. The theory of reading automaticity suggests that proficient recognition and decoding of words occurs when readers move beyond conscious and accurate decoding to automatic and accurate decoding. See, LaBerge D, & Samuels S A, "Toward a theory of automatic information processing in reading," Cognitive Psychology, 6, 293-323 (1974); Samuels, S. J. "Reading fluency: Its development and assessment," In A. E. Farstrup & S. J. Samuels (Eds.), What research has to say about reading instruction (3rd ed., pp. 166-183 (2002)); Stanovich, K. E., "Word recognition: Changing perspectives," In R. Barr, M. L. Kamil, P. Mosenthal, & P. D. Pearson (Eds.), Handbook of reading research, Vol. 2, pp. 418-452 (1991) New York: Longman. At the automatic fluent reading mode, readers do not have to examine closely or sound out most of the words they encounter; they simply recognize the words instantly and accurately on sight. Children are successful with decoding when the process used to identify words is fast and nearly effortless or automatic.

As noted, the concept of automaticity refers to a student's ability to recognize words rapidly with little attention required to the word's appearance. More so, readers have limited attention resources. If they have to continually consciously focus and allocate a large portion of their attentional resources to sight words' identification via the fast lexical route, those attentional resources will not be available to put to use for comprehension of the text. See, Coltheart M, Curtis B, Atkins P, Haller M, "Models of reading aloud dual-route and parallel-distributed processing approaches," Psychol Rev 100:589-608 (1993). In short, reading fluency bridges word sight recognition and decoding abilities with semantic comprehension of the text. At one end of this bridge, fluency connects to sight recognition automaticity and accuracy in decoding. At the other end, reading fluency connects to comprehension through prosody, or expressive interpretation. In short, when individuals cannot automatically and effortlessly recognize invariant properties of connected print text (e.g. shape, size, and color), their mastery of reading fluency is delayed or never accomplished.

Fluent reading also depends on how proficiently we handle visual spatial attention. Attention is a brain mechanism that enhances information processing at the attended location. Thus, attention operates as a filter removing irrelevant information from sensory-input streams. Rapid sight recognition of a letter within a string of connected letters, or a word within a text, seems to require a precise control of the spatial extent of the attentional focus to exclude irrelevant information. See, LaBerge D, Brown V, "Theory of attentional operations in shape identification," Psychol Rev 96:101-124 (1989). Brannan and Williams were the first to demonstrate that poor readers had problems with shifting attention from one target to another. See, Brannan J, Williams M, "Allocation of visual attention in good and poor readers," Percept Psychophys 41:23-28 (1987). Facoetti et al. showed several anomalies in dyslexic children at attentional control. They concluded that: a) dyslexics seem to have more diffused spatial attention; and b) dyslexics showed sluggishness of their automatic focusing of visual attention. See, Facoetti A, Molteni M, "The gradient of visual attention in developmental dyslexia," Neuropsychologia 39:352-357 (2001); Facoetti A, Turatto M, "Asymmetrical visual fields distribution of attention in dyslexic children: a neuropsychological study," Neurosci Lett 290: 216-218 (2000); Facoetti A, "Facilitation and inhibition mechanisms of human visuospatial attention in a non-search task," Neurosci Lett 298:45-48 (2001); Facoetti A, Paganoni P, Lorusso M L, "The spatial distribution of visual attention in developmental dyslexia," Exp Brain Res 132:531-538 (2000); Facoetti A, Paganoni P, Turatto M, Marzola V, Mascetti G G, "Visuospatial attention in developmental dyslexia," Cortex 36:109-123 (2000b); Facoetti A, Lorusso M L, Paganoni P, Cattaneo C, Galli R, Mascetti G G, "The time course of attentional focusing in dyslexic and normally reading children," Brain Cogni 53: 181-184 (2003a); Facoetti A, Lorusso M L, Paganoni P, Cattaneo C, Galli R, Umilta C, Mascetti G G, "Auditory and visual automatic attention deficits in developmental dyslexia," Cogn Brain Res 16: 185-191 (2003b); Facoetti A, Lorusso M L, Paganoni P, Umilta C, Mascetti G G, "The role of visuospatial attention in developmental dyslexia: Evidence from a rehabilitation study," Cogn Brain Res 15: 154-164 (2003c); Facoetti A, Lorusso M L, Cattaneo C, Galli R, Molteni M, "Multi-modal attentional capture is sluggish in children with developmental dyslexia," Acta Neurobiol Exp (Wars) 65: 61-72 (2005).

Vidyasagar and Pammer showed that the search time—size function increased more steeply for dyslexics than for normal in a serial search task. See, Vidyasagar T R, Pammer K, "Impaired visual search in dyslexia relates to the role of the magnocellular pathway in attention," Neuroreport 10: 1283 (1999).

These facts about visual attention and eye movement have been known for some time, but only recently have researchers begun to look at eye movement behavior and its implication to attentional demands and inhibitory neural control mechanisms as a reflection of cognitive processing during reading. See, Rayner K, "Eye movements, perceptual span, and reading disability," Annals of Dyslexia 33, 163-173, (1983). Research shows that saccade control and reading abilities depend on similar brain functions and show a parallel development. In other words, there is a correlation between the development of saccade control and reading abilities. Reading presupposes an accurate planning and control of ocular saccades and fixations. See, Morris R K, Rayner K, "Eye movements in skilled reading: implications for developmental dyslexia," In: Stein J F (ed) Vision and visual dyslexia. MacMillan Press, London, pp 233-242 (1991); Pavlidis G "Do eye movements hold the key to dyslexia?" Neuropsychologia 19:57-64 (1981).

Another goal of the present invention is to trigger mild-low physiological arousal in a subject. Research has found that different tasks require different levels of arousal for optimal performance. For example, difficult or intellectually demanding tasks may require a lower level of arousal (to facilitate concentration), but for unfamiliar, complex or difficult tasks, the relationship between arousal and performance becomes inverse, with a performance decline as arousal increases. Easterbrook states that an increase of arousal leads to a decrease in the number of spatial-temporal cues that can be utilized. See, Easterbrooke J A "The effect of emotion on cue utilization and the organization of behavior," Psychological Review, 66, 187-201, (1959). Indeed, it is well known that arousal (or stress) has negative effects on learning to read and on cognitive processes like attention (e.g., "tunnel vision"), memory and problem-solving.

In general, certain embodiments of the present invention teach the training of neural networks involved in promoting effortless automatic sight word recognition via the performance of a novel monotonous game-like task that stimulates optimal inhibitory control upon oculomotor, visuo-motor activity and selective cognitive executive functions that are mediated by the Pre-Frontal Cortex (PFC). Specifically, certain embodiments of the present invention teach how to technologically implement the conditions required to promote the inhibition of the involuntary control of ballistic eye movements that continually monitor the positioning and motor fluidity of hand & fingers' movements through the performance of the herein novel game-like task.

More so, certain embodiments of the present invention comprise of a novel game-like task aimed to bring about neuro-plastic changes that effect oculomotor, visuo-motor movement loops and cognitive control upon selective executive functions mediated by the PFC. We expect that the herein game-like task will bring about oculomotor and visuo-motor movement loops automaticity, free of attentional demands. The latter said is achieved by implementing a number of novel features, including a spatial-temporal kinematical activity, some perceptual constrains concerning both the structure of the non-verbal visual stimuli information and concerning internal performance-reward feedback strategies implemented via the herein game-like task in a number of performance challenging stages where the game-like task increases in difficulty.

Certain embodiments of the present invention teach a novel game-like task that generates a set of non-verbal visual stimuli parameters aimed to trigger fast neuro-plastic changes which promote neural inhibitory control resulting in self-regulation of oculomotor and visuo-motor loop movements' activity and selective cognitive executive function behaviors mediated by the PFC.

This novel non-verbal visual stimuli: 1) triggers mild to low physiological arousal (mild to low heightening of physiological activity); 2) promotes performance of attentional shifts as an aim in itself while downplaying attentional focus on target spatial-temporal parameters and object-like attributes (e.g. spotting, location, trajectory, kinematical state and attributes [such as planar (2D), color, shape, size, etc.]; 3) promotes inhibitory control upon shared neural network involving oculomotor, visuo-motor loop movements and selective cognitive behavior via triggering self-regulatory negative feedback loops.

All three characteristics of the above-said novel non-verbal stimuli of the herein game-like task accomplish attainment of effortless and automatic visual recognition of sight words. The present invention discloses a novel game-like task that enables a subject to effectively and rapidly promote the necessary physiological repertoire of sensory-motor-perceptual and selective cognitive controlled behaviors (e.g. attention shifts, gratification delay or relinquishment, mild to low heightening of physiological activity, etc.) in order to effortlessly and automatically recognize sight words that will grant a subject reading fluidity proficiency of connected text.

Another goal is to trigger mild to low physiological arousal in a subject. Certain embodiments of the present invention teach a novel game-like task that discloses selective sensory-motor kinematical goals such as: 1) Navigating a graphical planar mobile object, a "yellow car" for example, maintaining it as long as possible and as close as possible to the dividing line in the center of a road in which it travels; 2) In contradistinction to current computer/video games, there are no additional kinematical goals/demands involved in the navigation of the graphical planar mobile object/car (e.g. avoiding "obstacles", or disappearance and reappearance of the graphical planar mobile object/car from the visual display for a Δt); and 3) The herein disclosed graphical planar mobile object does not fulfill any additional kinematical functional requirements such shooting, jumping, flying, etc.

In accordance with an embodiment of the present invention, planar objects (such as the aforementioned "yellow car") are utilized. Planar objects are visualizations of graphical objects that lack perceivable depth (volume). Planar objects may be rendered by any graphical rendering process (e.g., 2D or 3D rendering) as long as they appear to be without any volume when displayed. However, one skilled in the relevant arts will appreciate that planar objects are discussed herein by way of example, and not limitation.

Still, another goal is to trigger mild-low physiological arousal in a subject. Certain embodiments of the present invention teach a novel game-like task that discloses visuo-motor activity consisting in: a) fast repetitive linear movements (i.e. along the horizontal "x" axis of the display, in left to right and right to left directions); and b) Repetitive eye-hand/fingers visuo-motor loops exercised in the same direction that our eyes and our hand/fingers move when reading or writing.

Still yet another goal is to trigger mild to low physiological arousal in a subject. Embodiments of the present invention teach a novel game-like task that discloses a number of selective perceptual-cognitive attributes: 1) In order to primarily allocate a subject's focus attention on rapid and effortless recognition of graphic planar objects, the herein game-like task is not displayed in "full screen"; rather, it is only displayed at the center portion of the screen (has surrounding limiting margins). Effortless allocation of focus attention in the center of the screen display is facilitated by an implicit perceptual expectation towards orienting our eyes to land at a point of spatial symmetry at a central location in the visual display; 2) the game-like task is displayed in a planar non-curvilinear surface. The solid angle and perceptual views of the game-like task are always the same; there are no close-ups or distant views compelling to change the angle of views, thus denying the user to perceptually experience a 3D space; 3) a non-visual stimulus of a graphic planar object depicting the shape of "road" borders moves from top to bottom (along the vertical "y" axis top-down direction) creating in the user a visual perceptual illusion of a graphic planar mobile object (e.g. a car) moving in a south to north direction; 4) the visual illusion of a vertically moving graphic planar mobile object in 3) takes place at a constant velocity; 5) the shape and size of the graphical planar objects in the game-like task remain constant during predefined time intervals; 6) in order to minimize distractions and effectively allocate focus attention to the task at hand, no new graphic objects appear suddenly into view on the road (e.g. cars, obstacles, etc.).

Certain embodiments of the present invention teach the training of the neural network involved in promoting effortless automatic sight word recognition via the performance of a novel game-like task that brings about an optimal inhibitory control upon oculomotor, visuo-motor loop movements and selective cognitive executive functions' mediated behaviors by the PFC. Specifically, certain embodiments of the present invention teach how a subject actuating the herein game-like task, gradually attains inhibitory control upon oculomotor, visuo-motor and selective cognitive executive functions' mediated behaviors by the PFC by adding increasing interactive "challenge display parameters", for i.e. the graphical implementation of weather conditions as rain or fog. These "challenging parameters" increase the execution difficulty of the visuo-motor eye-hand/fingers movement loops task by aiming to impede the user's visuo-motor navigation control of a graphic mobile object (e.g. yellow car) at the center of a road. These perceptual visual challenges are necessary in order to effectively guide a subject's performance to fall within an optimal motor-perceptual-cognitive range where inhibitory control can easily be promoted among oculomotor, visuo-motor loop movements and selective cognitive behaviors mediated by the PFC. The perceptual construction of such visual challenging conditions is achieved in such a way that the recognition of their spatial-temporal attributes will deny the priming of associative learning. Increasing the challenging parameters degree of difficulty includes at least one of: Rain—A 2D graphical representation of rain drops is superimposed on the spatial coordinates of the central region of the perceptual space. The rain drops decrease the visibility and manual navigability of the graphic planar mobile object on the road. The degree (size, shape, falling rate and color of rain drops) of visual obstruction is pre-defined. More so, the rain drops' size, shape, falling rate and color can be either constant or random; Fog—A 2D graphical representation of fog conditions superimposed on the spatial coordinates of the central region of the perceptual space. The degree of visual obstruction (fog concentration and photic luminosity) is pre-defined. More so, the fog concentration and photic luminosity can be either constant or random; Road shape appearance—increasing the number of sinusoidal road waves intensifies the wave-like appearance of the road increasing the navigability difficulty; graphic planar object velocity—gradual increase of the apparent graphic planar object velocity in stages. However, the velocity remains constant within each stage.

Still another goal of certain embodiments of the present invention is to teach a novel game-like task to promote visual spatial attentional shifts apportioning oculomotor and visuo-motor loop movement's performance selectively to either right or left brain hemisphere neural circuitry dominance. Specifically, if a subject's performance of the herein game-like task shows a higher internal score when: (a) the navigation took place in the area to the right of the road's center' dividing line in comparison to when (b) the navigation took place on the left side of the road, it then means that it is much easier for a subject to visually orient (attend novel events in the visual field), focus and process pattern recognition of non-verbal stimuli and exert control on visuo-motor loop movements via his left hemisphere (LH) neural circuitry. Neural networks distributed in the LH are responsible for processing stimuli information related to language (semantic information) and for storing it in memory. In the reverse situation in which a subject achieves a higher internal score when (b) versus (a), we can state that it is much easier for a subject to visually orient (attend novel events in the visual field), focus and process pattern recognition of non-verbal stimuli and exert control on visuo-motor loop movements, via his right hemisphere (RH) neural circuitry. Neural networks distributed in the RH are responsible for processing stimuli information related to spatial relationships of objects and to temporal aspects of novelty of events.

Oculomotor orienting, flexibility in shifting visual attention per se and subsequently sustaining attentional focus at the chosen spatial location to identify and process foveal and parafoveal targets (non-verbal and verbal stimuli) is an issue of high relevance for reaching mastery and competency of literacy in some languages. This is because in order to start reading a connected text, the visual stimuli is expected to be located at the far left margin of the page (to be preferentially processed by neural networks in the right hemisphere of the brain). On the other hand, as we continue reading and our eyes keep on sweeping the text towards the right direction, once they reach the middle half of the sentence and onwards, the text is preferentially processed by neural networks in the left hemisphere of the brain. As we approach the end of the sentence, our eyes perform a regressive ballistic movement and now land on connected text in the very beginning of the next sentence, again on the far left margin of the page.

Still yet another goal of certain embodiments of the present invention is to implement an internal "right predominant score" method, principally on the right visual field of a subject. The "right predominant score" covertly promotes an inhibitory behavior upon oculomotor, visuo-motor loop movements and selective executive cognitive behaviors mediated by the PFC. Orienting and sustaining focus attention on the RVF and actuating on the right side of the road, strongly correlates the game-like task performance to LH neural circuitry dominance. More so, we expect the novel game-like task herein taught to mainly trigger in a subject engaged in it, fast neural-plastic changes (neural activation) in the magno transient neural networks projecting dorsally from the visual occipital cortex to more specialized visual areas in the PPC. This resulting magno flow should bring about a fine tuning of visuo-motor control behavior which will improve eye-hand coordination movement loops' performance and consequently become one of the contributing factors promoting effortless and automatic visual recognition of sight words as well as reading fluency. Yet, the more a subject navigates the graphic planar mobile object in the right visual field on the right side of the road, the more the game-like task promotes oculomotor, visuo-motor and related selective PFC executive function cognitive inhibitory control among neural networks under the LH dominance. Hence, another key feature of the present invention is to facilitate visual orienting and focus attention sustenance on a subject's right visual field. The latter is achieved by, for example, shifting the dashed dividing line (supposedly representing the center of the road) slightly towards the left side of the road, increasing in such a way the width of the road portion located to the right of the dashed line, and further inducing a subject to navigate the graphic planar mobile object on the right visual field of the right side of the road.

Yet, another goal of certain embodiments of the present invention is to teach attainment of automatism upon oculomotor and visuo-motor movement loops behavior by a subject voluntarily performing a mild to intensive visuo-motor navigation activity in a novel game-like task, in a first stage. During such first stage, a subject actuates numerous fast repetitive eye-hand/fingers' movements in a relative short period of time. Such numerous repetitive right-left and left-right quick eye-hand/fingers' movements (for specific periods of time lasting approximately 63 sec), are performed while aiming to navigate a graphic planar mobile object (e.g. yellow car) and maintain it as close as possible to the dashed dividing line in the center of the road. This massive number of quick repetitive visuo-motor movement loops is processed and organized by the cerebellum, which receives in a brief time span, an overwhelming amount of (sensory-motor) practice effect information as well as motor learning training via sequential motor movements. Post finalizing a first voluntary navigation stage, a subject immediately begins a second stage where he/she voluntarily actuates low intensity navigation visuo-motor movement loops, in order to gradually decrease the visuo-motor activity, by smoothly and slowly navigating a graphical planar mobile object (e.g. a car) (this novel kind of navigation elicits ocular smooth tracking pursue of the graphical object) and accurately maintaining it on a central dividing line in a road. This second navigation stage, which consists of decreased visuo-motor movement loops activity, lasts for 21 seconds. Following this second visuo-motor voluntary navigation stage, a subject passively gazes at the center of the screen display. In this third stage, there is no interactive navigation visuo-motor activity, only passive oculomotor tracking movements. A subject's eyes passively track generated planar non-verbal stimuli that move across the screen on the center of the screen display. The smooth tracking of novel generated non-verbal stimuli generates in a subject a further inhibitory effect upon oculomotor and selective PFC executive function cognitive controlled neural networks, triggering parasympathetic activity, namely inducing a further calming effect that contributes to dropping arousal to mild to low levels. The third stage, consisting of oculomotor activity alone, lasts variably between 14 sec to 63 sec, in accordance with an embodiment of the invention. In the herein game-like task, stages 1, 2 and 3 are recurrent in a loop with no time delay gaps amongst them, for a minimum of 4 times and a maximum of 6 times, in accordance with an embodiment of the invention.

The implemented sequential motor learning training due to the novel performance of certain embodiments of the present invention minimizes the need to allocate attentional resources to the task at hand, thus capable of promoting neuroplasticity changes on neural networks in the cerebellum to accelerate the implementation a robust sensory-motor automatism in a subject.

Still, with the aim of triggering mild to low physiological arousal in a subject, certain embodiments of the present invention teach a novel game-like task that discloses the absence of a real-time feedback-reward display of a 'score' (represented as a number and/or text and/or symbol). The absence of a real-time score information is one of the key features of the present invention, purposely implemented in order to minimize at least one of: a) generation of mental stress (owing to a subject taxation of attentional resources due to sustained focus attention while performing numerous fast repetitive accurate as faceable possible eye-hand/fingers movement loops in a relatively short period of time); b) generation of physiological arousal by not providing explicit real-time information about actual performance status and; c) perceptual and cognitive eradication of a subject's desire to compete with himself/herself. More so, a subject performing the game-like task is not aware that the task at hand is covertly implementing a novel delay gratification reward strategy that tacitly correlates the real-time gradual attainment of a high "score" via interacting with perceptual-motor states of increasing difficulty (navigation challenges). The present novel game-like task aims to habituate a subject to forgo conscious real-time reward. Hence, as a direct consequence of a subject actuating the herein novel game-like task, we foresee that a subject will learn willingly to delay gratification for longer periods of time.

Certain embodiments of the present invention teach the promotion of effortless and automatic sight word recognition via the performance of a mild to low arousal novel game-like task. The present invention also teaches the performance of a game-like task that delays task gratification. The present invention generates novel non-verbal stimuli, which promotes attentional shifts, oculomotor and visuo-motor fast and repetitive movements' loops. The experience of performing the game-like task instigates strong neuroplasticity in a subject's brain, thus training a subject's oculomotor and visuo-motor movement's loops to allow for a rapid implicit acquisition of automatic skills necessary for the effortless mastery of sight word recognition. The herein invention accomplishes the latter by generating a visual flow of novel sensorial-motor-perceptual information aimed to promote automatic control of spatial visual attention and dorsal transient neural circuits responsible for eye movements, while also promoting inhibitory behavior of neural circuitry involving visuo-motor loops activity of the hand-fingers executing the task, particularly in a subject's left hemisphere's circuitry.

The present invention teaches the performance of a mild to low arousal innovative game-like task that, in complete contrast to entertaining/violent/educational computer/video games which include a great deal of 3D graphical objects moving in multiple kinematical trajectories on the computer screen and powerful graphical effects (with the purpose of making them more engaging and exiting), is described as "monotonous" since it does not trigger or induce: 1. Increase of aggressive thoughts, which in turn increase the likelihood that a mild or ambiguous provocation will be interpreted in a hostile fashion; 2. Increase of aggressive physical affect; 3. Increase of general physiological arousal (e.g. a sustaining long term increase in heart rate, blood pressure, respiration etc.) which tends to further promote the dominant emotional behavioral tendency; 4. Direct imitation of recently observed aggressive behaviors. See, Anderson C A & Bushman B J "Effects of violent video games on aggressive behavior, aggressive cognition, aggressive affect, physiological arousal, and prosocial behavior: A meta-analytic review of the scientific literature," Psychological Science, 12, 353-359, (2001).

In summary, the absence of explicit real-time feedback about actual performance elicits in a subject a perceptual-cognitive labeling about the nature of the novel game-like task as being monotonous, boring and, to some degree, gives a subject the overall subjective feeling about the global experience as not having been fun.

II. Design Goals

In view of the forgoing, it is desirable to provide a system that will promote effortless automatic sight word recognition of connected written text via delivery of novel non-verbal stimuli.

It is further desirable to provide a system that will promote effortless automatic sight word recognition via delivery of novel non-verbal stimuli triggering visual spatial attention shifts in order to enhance fast recognition and processing of verbal and non-verbal target stimuli in either the left or the right visual hemifield of a subject.

It is also desirable to provide a system that will promote effortless automatic sight word recognition via delivery of novel non-verbal stimuli promoting automatic inhibitory control of dorsal magnocellular transient neural networks, enabling accurate temporal planning of oculomotor movements, namely enabling smooth transitions between stable gaze and eye saccades.

It is additionally desirable to provide a system that will promote effortless automatic sight word recognition via delivery of novel non-verbal stimuli by executing a monotonous game-like task that consists in fast repetitive visuo-motor loops that strongly captivate the attentional focus of a subject in a manner that rapidly discriminates and processes salient features of a moving target(s), mainly in the fovea and parafoveal visual field. This motion-for-action novel visuo-motor loop activity task greatly diminishes reorienting towards competitive distracting sensorial stimuli in the peripheral visual field, particularly for in the RVF:

It is further desirable to provide a system that will promote effortless automatic sight word recognition of connected text via delivery of novel non-verbal stimuli targeting lexical processes underlying and contributing to reading fluency.

It is further desirable to provide a system that will promote effortless automatic sight words' recognition via delivery of novel non-verbal stimuli for the execution of tasks and/or game-like tasks where allocation of attentional resources will enable to focus in order to discriminate, process, retrieve and guide visuo-motor movement loops, while eliciting mild to low arousal in a subject.

It is further desirable to provide a system that will promote effortless automatic sight word recognition via delivery of novel non-verbal stimuli for the execution of tasks and/or game-like tasks that will delay immediate self-gratification (e.g. score) related to the game-task performance of a subject.

It is further desirable to develop new, assistive, educational and leisure devices (e.g. computer non-language/verbal educational software and computer games) which can assist preschoolers and beginner readers at home and in schools to make their first steps towards mastering the alphabetical code. Remedial teachers can introduce the present invention as a quick and easy assistive technology alongside their one-on-one phonological remedial teaching strategies, so it will help cognitive processes to mature and enable the meaning of words learning via phonological decoding strategies.

III. Exemplary Display Usage

In a preferred embodiment, the invention involves the display of a central area of a computer screen monitor, to perform a game-like task consisting of eyes-hand coordinated movement loops, for about 1 minute, followed by an eye-tracking task that takes place in the same setting. In an embodiment, a session consists in several consecutive repetitions of this pair of tasks.

Optionally, the required functionality is divided between a client and a server configuration, as schematically depicted in FIG. 1, although one skilled in the relevant arts will appreciate that other configurations can be utilized.

As shown in this FIG. 1, a client computer 200 comprises a screen monitor 100 where a Central Window (CW) Task Area 110 is displayed for the user to perform an Eye-Hand Coordination Task (EHCT) and/or an Eye-Tracking task (ETT). The relative size of this CW 110 is defined in the parameter configuration Module 330. In an embodiment, the CW 110 size could vary according to any selected random or predetermined function.

Figure 2:
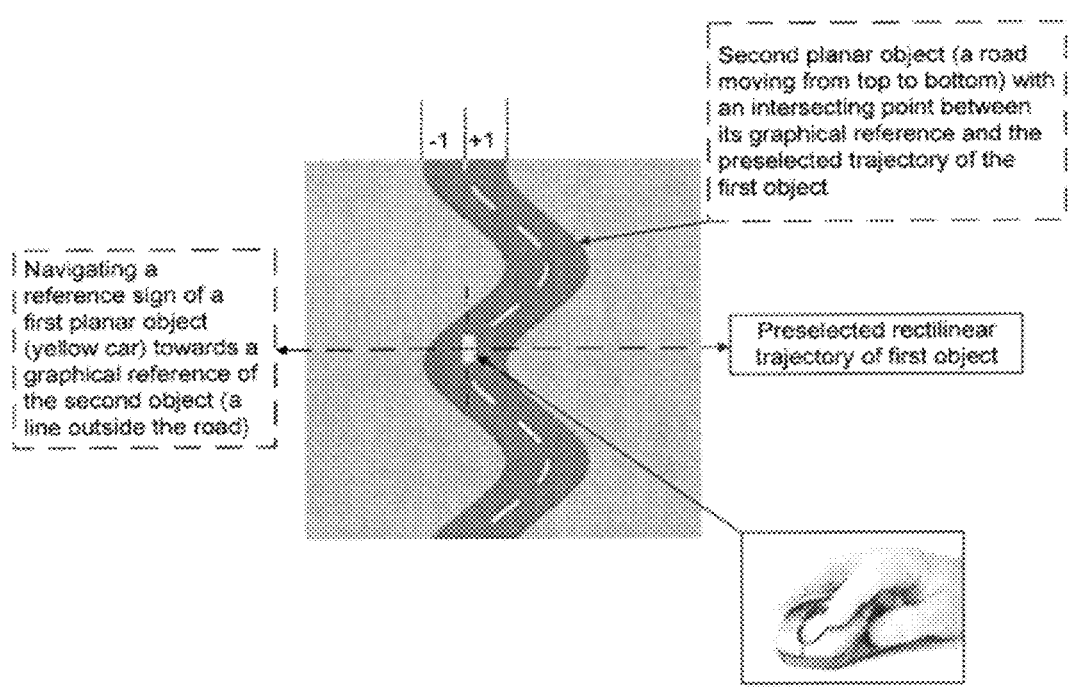
FIG. 2 is an exemplary block diagram of planar 1st and 2nd moving objects, in accordance with an embodiment of the present invention.

The game-like task consists of continually steering, along a preselected trajectory, the position of a reference sign, depicting a point or small area on visually planar mobile graphic object #1, to the point of intersection of this trajectory with a moving graphical reference marker, depicting a point or line on a visually graphic planar object #2, as shown in FIG. 2. The control of movement of graphic planar mobile object #1 is achieved by means of the computer mouse 500.

In an embodiment, the visually graphical planar mobile object #1 is a car with a yellow default color, and the visually graphical planar object #2 is a sinusoidal road moving downward in the CW 110, while graphical planar mobile object #1 is restricted to follow a trajectory along a horizontal line of movement, intersecting a central line of the moving road.

In an embodiment, a selected type of graphic planar mobile object #1 (from Library #6) conveys to the user a first non-verbal stimuli, while the type of graphic planar object #2 (selected from Library #5) conveys a second non-verbal stimuli to the user. The angular orientation of graphic mobile object #1 trajectory of movement, the central or not central line location of a graphic reference marker in graphic planar object #2 (selected from Library #12), the default color of graphic planar mobile object #1, are all defined in configuration Module 330, shown in FIG. 3, as a non-limiting example of an embodiment of the invention. The background color of graphic planar object #2, herein defined as the graphical space contained between the road pathway borderlines, and the color of the field herein defined as the graphical space outside the road borderlines, are also defined in the configuration Module 330. The non-verbal stimuli of graphic planar mobile objects #1 (from Library #6) may be a bird or a yacht as examples of mobile objects to be controlled by the computer mouse 500. Similarly, downward movement of graphic planar object #2 (from Library #5) may include a river or a canyon as examples of non-verbal stimuli.

In the above example, while the user has the optical impression of seeing the car moving vertically upward, he/she has to perform an eye-hand movement coordination loops in a task aimed to concur navigating the reference sign in a first graphic planar mobile object, (i.e. a car), towards the intersection point of its trajectory of movement, with the graphical reference marker of the second graphic planar object, the road (FIG. 2).

The faster the car seems to move upward, and the greater the amplitude of the borderline sinusoidal border of the road, the greater the difficulty to navigate the car at a minimal Δd distance between the car reference sign and the intersection of its trajectory of movement with the graphical reference marker of the road. Due to the pre-programmed movement of object #2, this intersection point will continually keep changing its position along the trajectory line of the car.

IV. Parameter Configuration

The velocity of the road and the amplitude of its wavy shape are only 2 of the presented possible parameters by which this invention can be implemented in order to control changes in the challenge presented to the user's ability to maintain the Δd value as close to zero as feasibly possible. In an embodiment, and as a non-limitative example, a number of Challenging Parameters (CP) are shown in Module 240 of FIG. 4, with a detail of a set of values used for an embodiment of this invention, for each one of 7 CPs.

The Module road length unit is herein defined as the pathway generated by one wavy shape of the borderlines of the road. This unit or module road length is herein called Path Way Module (PWM) and can take on different geometrical forms as exemplified in Library #5. In the preferred embodiment, a sinusoidal wave form for the PWM is used as a default, where other wave forms of the PWM could offer a different navigation challenge. The velocity challenge, in the example shown in Module 240, is given as the number of seconds required by 1 PWM to vertically move in the CW 110, a distance equal to its length unit.

In the preferred embodiment, the graphical reference marker inside the road is made up by points equidistant to the road's borders. Nevertheless, other possibilities are shown in Library #12, as indicated in configuration Module 330 in FIG. 3.

A preferred embodiment consists of 7 challenge parameters configurations of Module 240 ($CP_n$ levels) each one implemented by different sets of 9 variable parameters. Each of the 7 challenge variables configurations consists in a particular set of variable parameter values depicting increasing levels of difficulty for the user to navigate a car at the lowest Δd value feasible possible. The challenging parameter consists in the 7 sets of variables herein designated as $CP_n$ (n=0, 1, 2, 3, 4, 5, 6).

The 2 variables parameters in Module 240 depicting density of the rain and/or fog can be regulated by software means to produce different challenge levels by known means in computer graphics.

V. Adaptability to User Performance

The game-like task of this invention starts at a relative low level of difficulty and can be predefined for different user populations, depending, for example, on age, learning disability, particular time of the day in the circadian cycle when the game-like task is performed, as well as conditions associated with developmental maturational factors. In the preferred embodiment, the first starting level of difficulty is designated as $CP_0$, characterized by a particular and predefined set of variable parameters specified on Module 240 in FIG. 4. The other 6 sets of challenging parameters for increased levels of difficulty $CP_1$, $CP_2$, $CP_3$, $CP_4$, $CP_5$, $CP_6$ are also specified in Module 240, as shown in FIG. 4, as a not-limitative example of challenging parameter configurations.

The eyes-hand motor coordination movement task is executed during discrete time intervals denominated Active Resting Cycles (ARC) which last 84 seconds in the preferred embodiment, as shown in Module 330 of FIG. 3. In an embodiment the end-goal task challenge consisting in keeping the car's position in the road central line shown in FIG. 2 to endure for the first and active 63 seconds of this period. In the last 21 seconds of the ARC, the values of the CP parameters are greatly reduced, making these last 21 seconds equivalent to a quasi-resting sub-period. In an embodiment, this CP parameters' reduction consists in the decrease of CP values to a 25% of the $CP_0$ values with no additional challenging parameters presented to the user. One skilled in the relevant arts will appreciate that the values provided herein for parameters such as ARC and CP values are given by way of example, and not limitation, and can be adjusted accordingly to the situation.

During the entire active 63 seconds period, and at each 100 msc interval, the Δd distance is measured. Based on the 630 measurements of this active ARC period, the Module 210 of FIG. 5 executes a calculation of the Game Raw Score in the sub-Module 211, using the following algorithm:

$$\text{Game Raw Score}(GS) = \frac{1}{\sqrt{\text{mean }\sum \Delta d^2}} \times \frac{63000 - te}{63000} \times \frac{1}{SCF} \quad (1)$$

Where the is a parameter depicting the total time the car center is outside the road borderlines, measured in milliseconds. The value of the Δd could be obtained by gauging the number of screen pixels making up the Δd distance from the road reference marker to the car reference sign. As example of extreme values for GS, if Δd approaches the zero value, GS approaches infinite; if the value of the to parameter approaches 63000 milliseconds, GS will tend to approach the zero value.

For calculation purposes, Δd is a value between 0 and 1 or between 0 and (−1) for when the center of graphic planar object #1 is at the right or left side of a graphical reference marker, like a center dashed line inside the road respectively, as shown in FIG. 2

$$\text{Then: } 0 \leq |\Delta d| \leq 1 \quad (2)$$

The value of Δd is obtained from the quotient between (i) the number of screen pixels found between the reference sign of graphic planar mobile object #1 and the intersection point and (ii) the number of pixels found between the road's graphical reference marker (at the intersection point) and the right or left borderlines of the road. The SCF is a score correction factor which compensates for the reduced value of Δd for same pixel distances to the reference marker due to greater values of the road amplitude for CPs other than $CP_0$. By way of non-limiting example, for $CP_0$, $SCF_0=1$, and for $CP_n$, $SCF_{1-6}>1$.

Figure 5:
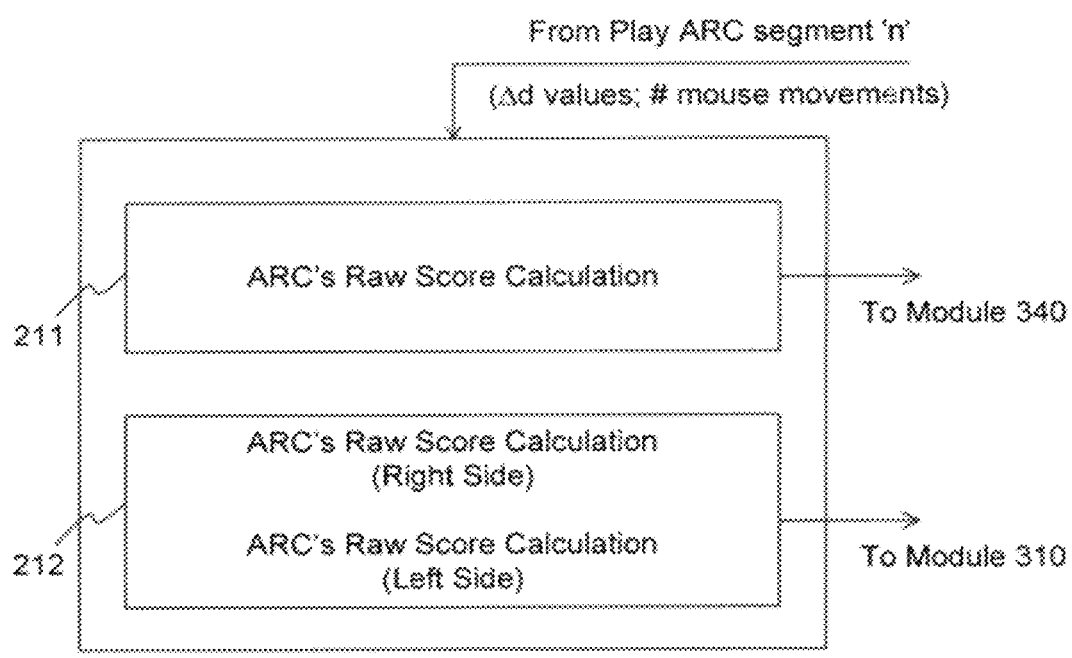
FIG. 5 is a block diagram of Module Raw Scores Calculation, in accordance with an embodiment of the present invention.

Before the end of an ARC, the GS value, calculated at sub-Module 211 of FIG. 5, is sent to Module 340, which defines the ARC progression inside a session by sub-Module 341. Module 340 also defines by sub-Module 343 and 344 the session's progression inside a predefined program or the tandem of sessions to be executed during a predefined number of days.

VI. Exemplary Session Details

In a preferred embodiment, a session contains a total of 4 ARCs lasting 84 seconds each, where each ARC is followed by an eye tracking task performed during a post-ARC time segment. In the first session of a program, the eye-tracking task time segment will be of 81 seconds, as stated in Module 330 of FIG. 3. Hence the total duration of a session is of 660 seconds.

Figure 6:
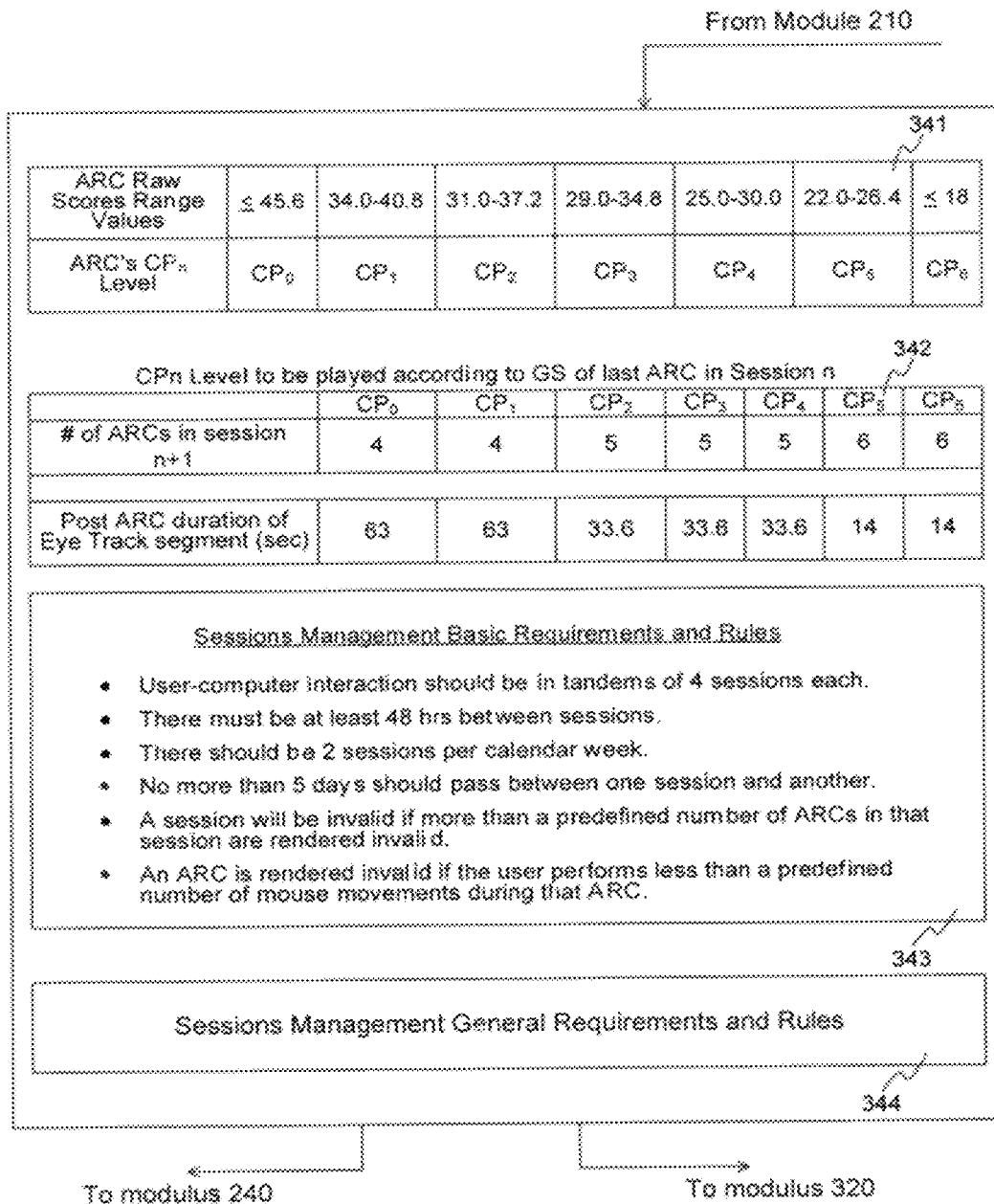
FIG. 6 is a block diagram of Module ARC and session progression, in accordance with an embodiment of the present invention.

Depending on the GS value obtained in Module 340, the following ARC to be played by the user in a session will be configured with a $CP_n$ set of variable parameter values defined in the sub-Module 341 shown in FIG. 6 which is herein shown as a non-limitative possibility example.

As a general rule, the user will continue playing at a $CP_n$ level in following ARCs until the GS obtained for the played ARC will be higher than the maximal range value assigned to that specific $CP_n$, or the GS obtained for the played ARC will be lower than the minimal value in that specific $CP_n$, range. In the former case, the user will play at a higher level of difficulty at $CP_{n+1}$ level in the subsequent ARC, and will drop a level of difficulty and play at the $CP_{n-1}$ level in the last case.

If the user achieves a GS score value of 47, for example, (a GS value higher than the assigned maximum of 45.6) at the initial $CP_0$ level, in the next ARC, the user will engage in a game-like task that has been configured according to the $CP_1$ level of higher difficulty, where the range of potential raw scores is of lower GS values (34.0-40.8) than those GS values which could have been attained at the easier performance $CP_0$ level.

In a preferred embodiment, the CP for the first ARC of a session is always played at the $CP_0$ level.

In a preferred embodiment, depending on the GS obtained by Module 340 for the last ARC played of any session, 2 parameters will be defined for the configuration of the following session in a program, as follows:
  i. The $CP_n$ of the 2nd ARC in accordance with sub-Module 341 of FIG. 6
  ii. The number of ARCs the user will play in the following session, which is shown in sub-Module 342 of FIG. 6.

In the preferred embodiment, the total time of the session is kept under 11 minutes (660 seconds). As the number of ARCs per session increases in direct correlation with the EHCT played at higher CP levels, the ETT will take place along shorter time segments, as indicated in sub-Module 342 of FIG. 6.

In this post-ARC eye tracking task, the user's eye is enticed to follow the movement of a non-verbal stimuli object #3, which emerges from one side of the CW 110, and follows a horizontal sequential kinematical path in the direction the user reads and writes, disappearing behind the opposite side of the CW 110. In a preferred embodiment, this sequential kinematical movement follows a left to right trajectory path, where it vanishes to reappear again emerging from the left side of the CW 110. In a preferred embodiment, these trajectory paths will resemble the display lines of a text in a book or a newspaper. Starting on the upper part of the CW 110, each following trajectory path will emerge from a lower point than the previous trajectory path on the left side. Non-verbal stimuli object #3 will sequentially keep moving through the kinematical line trajectories, until some predefined lower line limit position and start back again from the upper trajectory line position, if the time length of the post-ARC segment will allow it.

About 4 seconds before the next ARC begins (if there is a next ARC), moving object #3 starts to blink in order to signal the user the upcoming start of the navigation period of non-verbal stimuli graphic mobile planar object #1 during the ARC EHCT task. Module 330 will indicate the shape of non-verbal stimuli object #3 from a library of shapes #7, as well as its color and its kinematical parameters, which define its movement across the CW 110.

In a preferred embodiment, the eye tracked moving Non-verbal stimuli object #3 decelerates its speed along its kinematical trajectory path from the left end of the CW 110 until it vanishes on the right end of the CW 110. The kinematical parameters shown in the configuration file of Module 330 will consist in a velocity parameter value V3 and an acceleration parameter value $g_3$. The traveled space S of object #3 across the CW 110 will be:

$$S = V_3 t - g_3 \cdot t^2 \quad (3)$$

Only one at a time kinematical linear trajectory path of object #3 will be eye-tracked by the user.

If FIG. 7, an example of higher and lower linear trajectory path in a CW 110 is shown, where moving non-verbal stimuli object #3 consists in a square icon form. In an embodiment, the distance between linear trajectory paths is 2% of the height screen resolution. This eye-tracking task can be accomplished in many different forms by for example, choosing different shapes for moving object #3, different vertical separations between linear trajectory paths and different values for the velocity and acceleration parameters. The above example is for the preferred embodiment.

Computers provide a series of time values generally known as interrupts, associated with the movement of the mouse pointer on the screen, indicating if the mouse pointer is changing or not its 'x, y' coordinates' location values on the screen monitor.

Figure 8:
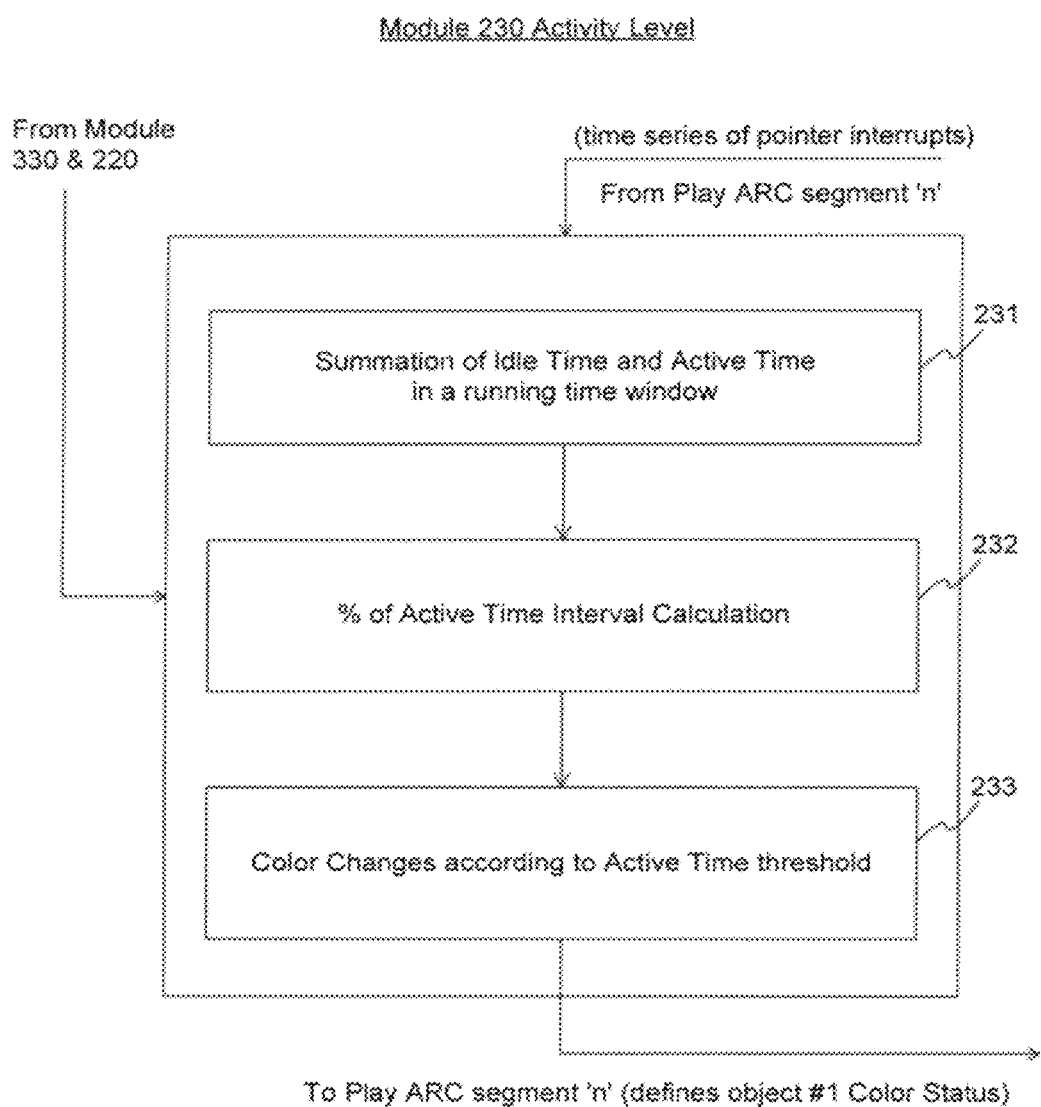
FIG. 8 is a block diagram of Module Activity Level, in accordance with an embodiment of the present invention.

The activity level Module 230 of FIG. 8 provides a mechanism by which, if the number of interrupts and/or smoothness in the mouse movements decreases below some predefined activity threshold shown in Module 330, the graphic planar mobile object #1 changes its default color from yellow to the red color. In addition, if the mouse movements become increasingly smoother and the number of interrupts surpasses some predefined activity threshold shown in Module 330, graphic planar mobile object #1 changes its default color from yellow to blue.

Computer time data of interrupts (Tint) is produced as long as graphic planar mobile object #1 (to which the pointer is fixed) keeps moving on the screen. If graphic planar mobile object #1 stops and starts moving again, the produced time series of Tint data will present a time gap (Tg) between the computer clock time when graphic planar mobile object #1 actually stopped and the computer clock time when graphic planar mobile object #1 started moving again. Differences between external clock's time data and computer's clock time data will most likely exist due to the computer time processing granularity which, depending on the computer, could be in the order of 20 msc.

On a non-limitative example of how mouse movement can be quantified in real time, in order to provide a desired feedback to the user, Activity Level Module 230 shown in FIG. 8 has been configured in accordance to the method and algorithms which are now described.

i. Produce an array of time gaps $T_{gn}$ ($T_{g1}$, $T_{g2}$, $T_{g3}$ ... $T_{gn}$).
ii. Define an idle threshold time value $T_L$, which will depend on the $CP_n$ level at which graphic planar mobile object #1 is navigated by the user ($T_{Ln}$).
iii. In a running time window of 3000 milliseconds, calculate total idle time for this window ($TT_{idl}$).

$$TTidl = \Sigma T_g - T_{Ln} \text{ for all } T_g > T_{Ln} \quad (4)$$

iv. The active time of the user ($T_a$) in milliseconds during the running window will be:

$$T_a = 3000 - TTidl \quad (5)$$

v. Calculate the percentage of user's active time $T_a$, in the running window as:

$$\% T_a = \frac{T_a}{3000} \cdot 100 \quad (6)$$

vi. Repeat steps i) to v) at each 1000 milliseconds.

The value of $T_{Ln}$ depends on the ordinal value of n in the $CR_n$ as follows:

$$T_{Ln} = 110 - 10 \cdot n \quad (7)$$

The graphic planar mobile object #1 turns red if: % $T_a \leq 55\%$ (according to Module 330)

The graphic planar mobile object #1 turns green if: % $T_a \geq 70\%$ (according to Module 330)

In a preferred embodiment, raw scores obtained by users playing the herein game-like task are analyzed in order to provide a non-real time feedback to the user, to keep him/her informed of performance and changes in personal parameter values of relevance and important for statistical studies about responses of different populations after the use of this system.

Because the EHCT is played at different levels of difficulty, raw scores are individually normalized in relation to the particular difficulty that each user confronts at the lowest $CP_0$ difficulty level.

Figure 9:
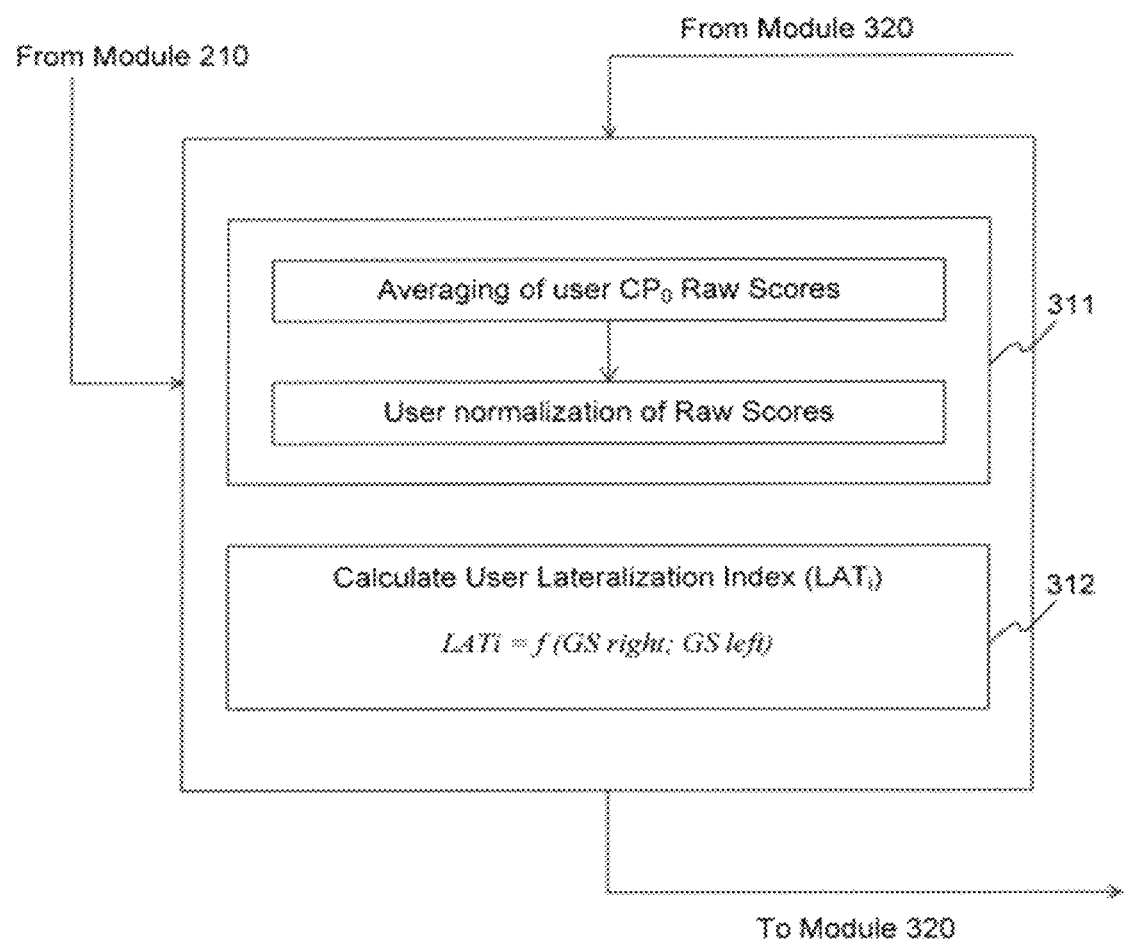
FIG. 9 is a block diagram of Individual Score Performance Calculation Module, in accordance with an embodiment of the present invention.

In an embodiment, the Game Raw Score (GS) obtained in an ARC with algorithm
(1) is individually normalized by Module 310 shown in FIG. 9 by the following method:

i. A reference Normalize Game Score ($NGS_0$) is calculated by averaging all GS values obtained during the 1st and 2nd sessions in ARCs that were played at $CP_0$ by a user.

$$NGS_o = \text{Avg GS at CP0 (for 1st and 2nd session)} \quad (8)$$

The obtained individual reference value GSo will be valid for a number of sessions in a predefined program. The GSo value is calculated by sub-Module 311 of FIG. 9.

ii. Per each individual user, a normalization coefficient $NCoef_n$ for a GS played at that particular session at $CP_n$ (n=1 to 6), will be $$NCoef_n = \frac{NGS_0}{\text{Avg}\Sigma GS_n} \quad (9)$$

Where $GS_n$ are the raw scores of ARCs played at $CP_n$ in that particular session iii. The $NCoef_n$ of a particular session according to (ii) will be saved in the Database Memory Module 320 of FIG. 1 and used to calculate the normalized score of ARCs played at $CP_n$ in that particular session or in future sessions of a predefined program. Normalized game scores for each ARC played at $CP_n$ ($NGS_n$) are calculated by Module 311 of FIG. 9.

$$NGS_n = NCoef_n \cdot GS_n \quad (10)$$

In addition to calculating the GS for user performance across the area depicting the total width of the road from one borderline to the other along the rectilinear pathway of non-verbal stimuli graphic planar mobile object #1, we can also calculate the GS for the user performance on the right side ($GS_{right}$) and on the left side ($GS_{left}$) of the road pathway separately.

$$GS_{right} = \frac{1}{\sqrt{\text{mean }\Sigma(\Delta d_{right})^2}} \times \frac{63000 - te_{right}}{63000} \times \frac{1}{SCF} \quad (11)$$

$$GS_{left} = \frac{1}{\sqrt{\text{mean }\Sigma(\Delta d_{left})^2}} \times \frac{63000 - te_{left}}{63000} \times \frac{1}{SCF} \quad (12)$$

Where $te_{right}$ is the value representing the time spent on the right side of the road and $te_{left}$ is the value representing the time spent on the left side of the road respectively.

When these values are calculated by sub-Module 312 of FIG. 9, it is possible to obtain the user's lateralization index ($LAT_i$) as a function of $GS_{right}$ and $GS_{left}$.

$$LAT_i = f(GS_{right}, GS_{left})$$

The value of $LAT_i$ can be calculated in two algorithmic ways as $$\frac{GS_{right}}{GS_{left}}$$

or also as $$\frac{2GS_{right}}{GS_{right} + GS_{left}}.$$

In the preferred embodiment, the second algorithmic way is implemented, and calculated by sub-Module 312 of FIG. 9.

The normalized game scores of individual users and their lateralization indexes are stored in the Database Memory Module 320 of FIG. 1.

In between sessions time intervals follow a number of requirements and rules, implemented by Module 340, at its sub-Module 343 and 344, as shown in FIG. 6.

At the end of a session, the user receives a screen message informing him/her when he/she are recommended to execute the following session.

Figure 10:
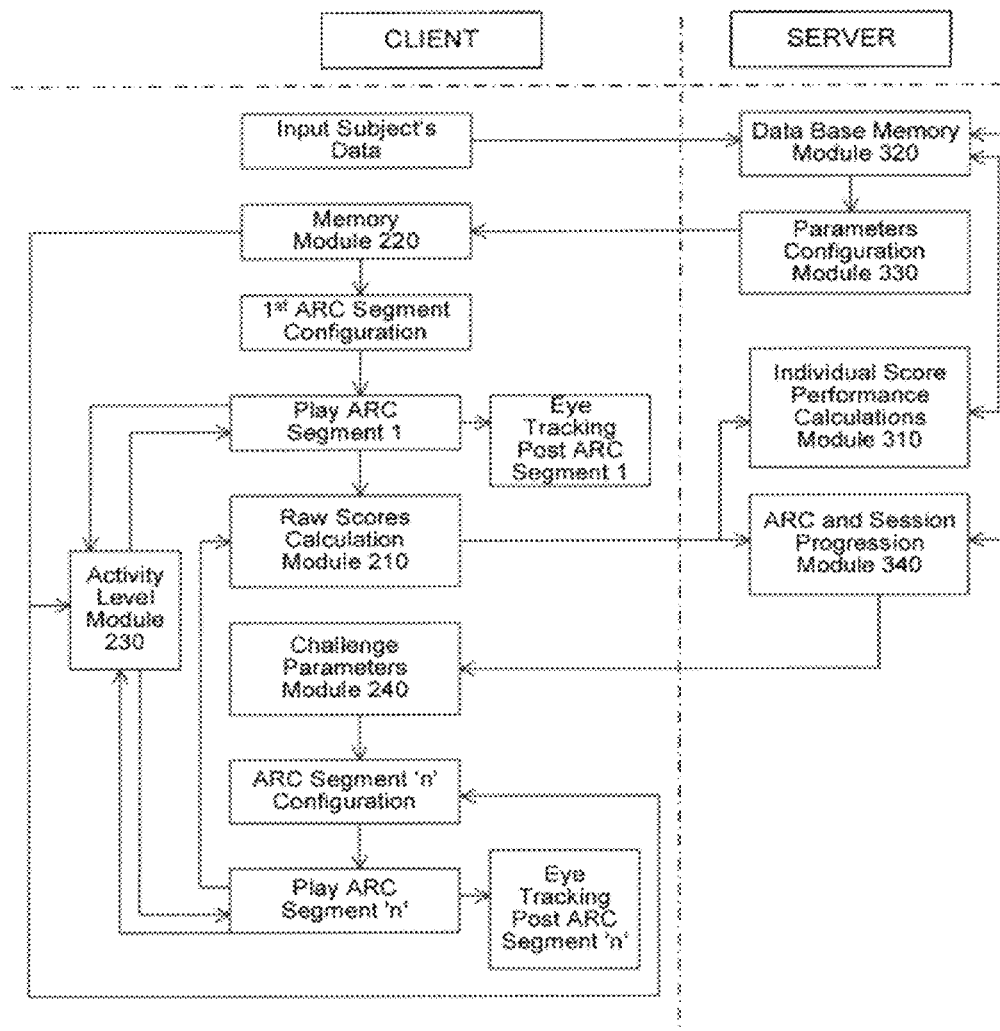
FIG. 10 is a Functional Steps Flow Chart of a Session, in accordance with an embodiment of the present invention.

FIG. 10 is a flowchart showing functional steps by which a single session of the herein invention is performed, in accordance with an embodiment of the present invention. One skilled in the relevant arts will appreciate that inventive aspects of the present invention may be accomplished by a subset of the steps depicted in the flowchart of FIG. 10, and the precise steps shown in FIG. 10 are provided by way of example, and not limitation.

By means of the keyboard 400 of FIG. 1, the user will introduce in the system's Database Memory Module 320 of FIG. 10, any required data for the session to be performed, as predefined in the user's manual and/or showing up on screen monitor 100 of FIG. 1. Data of the user stored in Database Memory Module 320 of FIG. 10 together with related user's parameters obtained from Module 310 of FIG. 9 and Module 340 of FIG. 6 after completion of 1st ARC of 1st session, are sent to the Parameters Configuration Module 330 of FIG. 3, which in turn will send particular required parameters to Memory Module 220 of FIG. 1, in order for the required ARC of that particular session to be configured.

The first ARC of any session is configured according to challenge parameters corresponding to $CP_0$, but the 2nd ARC configuration of the 1st session depends on the raw score obtained by the user in the first ARC, whereas the 2nd ARC of all the following sessions in a predefined program, depends on the raw score obtained in the last ARC of the previous session.

After playing the eye-hand movements' coordination task during an ARC, the user will engage in an eye-tracking task, immediately followed again by an ARC playing the eye-hand movements' coordination task for a time specified in Module 340 of FIG. 6. While playing the eye-hand movements' coordination task with the mouse, Activity Level Module 230 of FIG. 8 provides the user with real time feedback information of his/her hand's movements. While the default color of the car is yellow, under some predefined activity threshold the car will turn red if the user does not continuously move the mouse and/or does not navigate the car smoothly. Above some predefined activity threshold level of navigation smoothness and/or continuity in the mouse movements, the car will turn blue. In an embodiment, feedback is provided each second, based in the user's navigation performance during the previous 3 seconds.

For each ARC, raw scores are calculated by Module 210 of FIG. 5, which sends the calculated values to ARC and Session Progression Module 340 of FIG. 6 according to which is determined if the following ARC played by the user will remain or not at the same CP level), which in turn sends information to Challenge Parameters Module 240 of FIG. 4.

At the end of a session, the user will receive a recommendation on his computer screen, regarding the suggested optimal time schedule range for him/her to engage in the next session. This individual, customized user scheduled program, is performed by ARC and Session Progression Module 340 of FIG. 6. Personal user feedback performance information about his/her normalized raw score and changes in his/her lateralization index, can be obtained by a Printer Module 600. The printed data about his/her personal performance data it is stored in Database Memory Module 320 of FIG. 1, which was previously received from Individual Score Performance Calculations Module 310 of FIG. 9.

VII. Example Computer System Implementation

Figure 11:
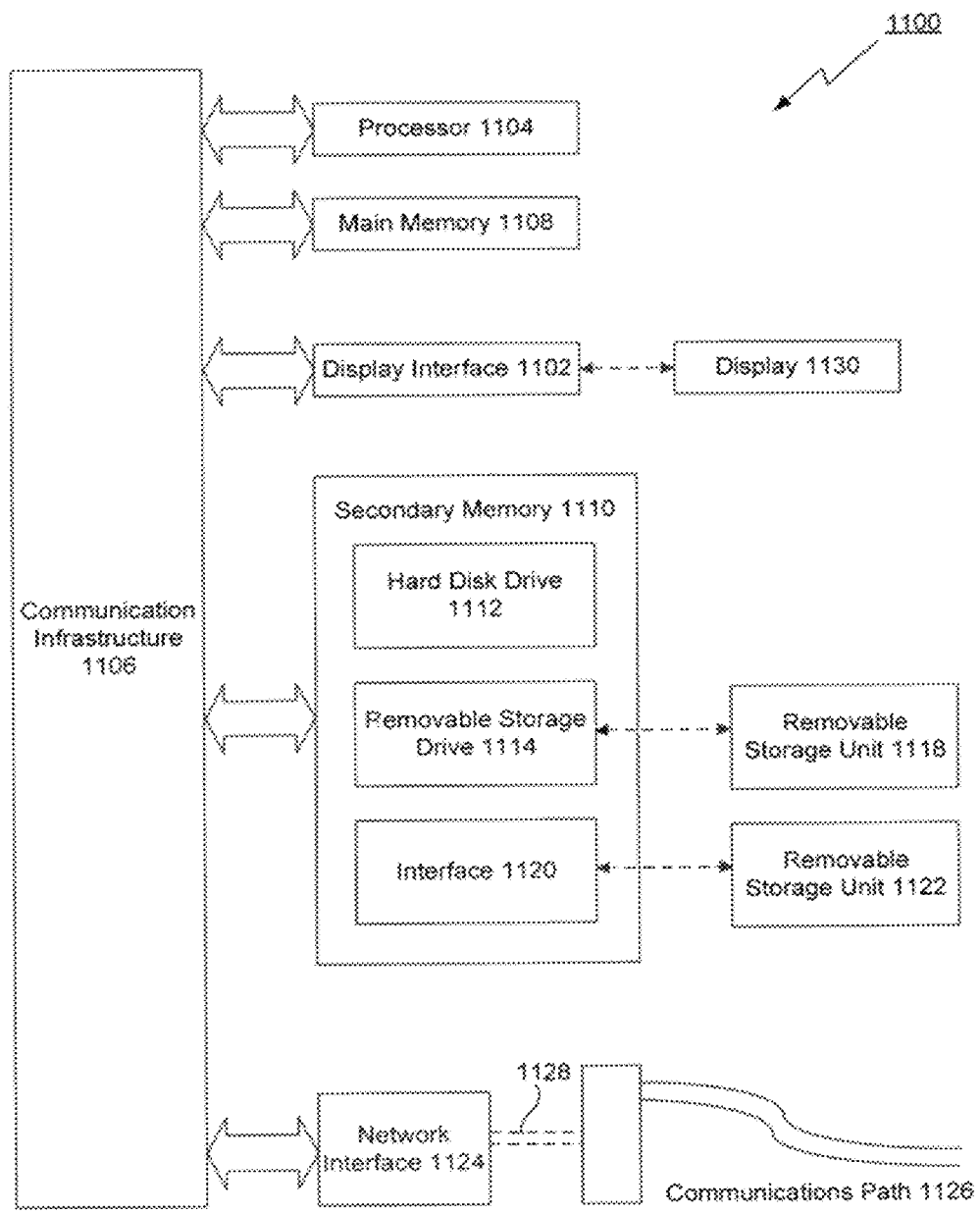
FIG. 11 depicts an example computer system in which embodiments of the present invention may be implemented.

Various embodiments and portions thereof of the present invention can be implemented by software, firmware, hardware, or a combination thereof. FIG. 11 illustrates an example computer system 1100 in which the present invention, or portions thereof, can be implemented as computer-readable code. For example, the behaviors of the modules in FIG. 1 and the flowchart of FIG. 10 can be implemented in system 1100. Various embodiments of the invention are described in terms of this example computer system 1100. After reading this description, it will become apparent to a person skilled in the relevant art how to implement the invention using other computer systems and/or computer architectures.

Computer system 1100 includes one or more processors, such as processor 1104. Processor 1104 can be a special purpose or a general purpose processor. Processor 1104 is connected to a communication infrastructure 1106 (for example, a bus or network).

Computer system 1100 also includes a main memory 1108, preferably random access memory (RAM), and may also include a secondary memory 1110. Secondary memory 1110 may include, for example, a hard disk drive 1112, a removable storage drive 1114, and/or a memory stick. Removable storage drive 1114 may comprise a floppy disk drive, a magnetic tape drive, an optical disk drive, a flash memory, or the like. The removable storage drive 1114 reads from and/or writes to a removable storage unit 1118 in a well-known manner. Removable storage unit 1118 may comprise a floppy disk, magnetic tape, optical disk, etc. that is read by and written to by removable storage drive 1114. As will be appreciated by persons skilled in the relevant art(s), removable storage unit 1118 includes a computer usable storage medium having stored therein computer software and/or data.

In alternative implementations, secondary memory 1110 may include other similar means for allowing computer programs or other instructions to be loaded into computer system 1100. Such means may include, for example, a removable storage unit 1122 and an interface 1120. Examples of such means may include a program cartridge and cartridge interface (such as that found in video game devices), a removable memory chip (such as an EPROM, or PROM) and associated socket, and other removable storage units 1122 and interfaces 1120 that allow software and data to be transferred from the removable storage unit 1122 to computer system 1100.

Computer system 1100 may also include a communications interface 1124. Communications interface 1124 allows software and data to be transferred between computer system 1100 and external devices. Communications interface 1124 may include a modem, a network interface (such as an Ethernet card), a communications port, a PCMCIA slot and card, or the like. Software and data transferred via communications interface 1124 are in the form of signals that may be electronic, electromagnetic, optical, or other signals capable of being received by communications interface 1124. These signals are provided to communications interface 1124 via a communications path 1126. Communications path 1126 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 1118, removable storage unit 1122, and a hard disk installed in hard disk drive 1112. Signals carried over communications path 1126 can also embody the logic described herein. Computer program medium and computer usable medium can also refer to memories, such as main memory 1108 and secondary memory 1110, which can be memory semiconductors (e.g. DRAMs, etc.). These computer program products are means for providing software to computer system 1100.

Computer programs (also called computer control logic) are stored in main memory 1108 and/or secondary memory 1110. Computer programs may also be received via communications interface 1124. Such computer programs, when executed, enable computer system 1100 to implement the present invention as discussed herein. In particular, the computer programs, when executed, enable processor 1104 to implement the processes of the present invention, such as the steps in the methods illustrated by the behaviors of the modules in FIG. 1 and the flowchart of FIG. 10, discussed above. Accordingly, such computer programs represent controllers of the computer system 1100. Where the invention is implemented using software, the software may be stored in a computer program product and loaded into computer system 1100 using removable storage drive 1114, interface 1120, hard drive 1112 or communications interface 1124.

The invention is also directed to computer program products comprising software stored on any computer useable medium. Such software, when executed in one or more data processing device, causes a data processing device(s) to operate as described herein. Embodiments of the invention employ any computer useable or readable medium, known now or in the future. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, optical storage devices, MEMS, nanotechnological storage device, etc.), and communication mediums (e.g., wired and wireless communications networks, local area networks, wide area networks, intranets, etc.).

VIII. Conclusion

It is to be appreciated that the Detailed Description section, and not the Summary and Abstract sections, is intended to be used to interpret the claims. The Summary and Abstract sections may set forth one or more but not all exemplary embodiment of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A computer-implemented method for producing interactive visuo-motor and/or interactive oculomotor non-verbal stimuli in a subject, the method comprising:
    displaying a first visualization of first and second graphical objects on a display communicatively coupled with one or more processors, the first graphical object having a first color, and the second graphical object comprising a pathway having a geometric wave form and a graphical reference marker equidistant from a left and a right borderline of the pathway, wherein the pathway is defined by a parameter;
    receiving, via an input device communicatively coupled with the one or more processors, a command from a user to change a display position of the first graphical object, wherein the command is based on visuo-motor voluntary control of the user;
    changing a display position of the first graphical object on the display according to an application of kinematical predefined rules to the command from a first display position to a second display position;
    determining, on the one or more processors, a new value of the parameter based on a normalized performance score for the user, wherein the form of the pathway defined by the second graphical object changes based on the normalized performance score for the user, wherein the normalized performance score for the user is determined based on the second display position of the first graphical object relative to the graphical reference marker;
    determining, on the one or more processors, a second visualization of the first and second graphical objects, based at least on the second display position of the first graphical object, and the pathway defined by the determined new value of the parameter,
    wherein the second visualization of the first graphical object comprises a second color of the first graphical object, the second color being selected based on an idle time of the subject compared with a predetermined idle threshold time value, the idle time being determined based on aggregation of a plurality of time gaps between arrival times of consecutive interrupts received at the one or more processors from the input device; and displaying, on the display, the second visualization of the first and second graphical object.

2. The method of claim 1, further comprising:
modifying the parameter during a session in accordance with the normalized performance score for the user on a previous predefined time interval.

3. The method of claim 1, wherein the parameter comprises kinematical parameters configured to allow a subject's eyes to voluntarily track the graphical reference marker relative to the display position of the first graphical object.

4. The method of claim 1, wherein the display position of the first graphical object is changed under visuo-motor voluntary control of the subject using a mouse.

5. The method of claim 1, wherein displaying the first visualization of the graphical object on the display comprises displaying a first graphic mobile planar object configured to move along a predefined area of the second graphical object represented as a second graphic mobile planar object.

6. The method of claim 5, wherein the graphical reference marker is depicted inside the predefined area of the second graphical object.

7. The method of claim 5, wherein the predefined area of the second graphical object has a graphical form of the pathway.

8. The method of claim 1, wherein the first graphical object is selected from a group of graphic mobile objects comprising a car, a bird, a panther, and a yacht.

9. The method of claim 1, further comprising:
providing sensorial feedback information to the subject comprising a degree of navigation smoothness of the first graphical object.

10. The method of claim 1, wherein the visualization of the second graphical object comprises changes in graphical and/or kinematical parameters provided in accordance with a predefined program.

11. The method of claim 1, wherein changes to a trajectory of the first graphical object comprise changes to aim the trajectory of the first graphical object to intersect the graphical reference marker of the second graphical object.

12. The method of claim 1, further comprising:
computing a linear distance between the first and second graphical objects, the linear distance based on a distance between a reference sign of the first graphical object and the graphical reference marker of the second graphical object.

13. The method of claim 12, further comprising:
computing the normalized performance score for the user during a predefined time interval using the linear distance between the first and second graphical objects during the predefined time interval.

14. The method of claim 1, wherein the second graphical object defines a pathway for movement of the first graphical object.

15. The method of claim 1, wherein the second graphical object is selected from a group of graphical objects comprising a road, a river, and a canyon.

16. The method of claim 1, wherein changing the parameter of the geometric wave form of the pathway defined by the second graphical object comprises:
changing parameters of a sinusoidal form of the pathway defined by the second graphical object.

17. The method of claim 1, wherein the parameter comprises graphical and kinematical parameters of the second graphical object.

18. The method of claim 17, further comprising:
changing the graphical and/or kinematical parameters of the second graphical object to present different difficulty levels.

19. The method of claim 1, further comprising:
correlating the normalized performance score for the user during a time interval with a difficulty level for the time interval; and
changing a difficulty level for a subsequent time interval based on the correlation.

20. The method of claim 1, wherein the graphical reference marker splits the second graphical object into equally-proportioned sides.

21. The method of claim 1, wherein the graphical reference marker splits the second graphical object into differently-proportioned sides.

22. The method of claim 1, wherein the first and second graphical objects are displayed during a time interval, wherein the time interval is in harmonic relationship with a day cycle.

23. The method of claim 22, wherein the harmonic relationship is represented by a time interval of 84 seconds.

24. The method of claim 1, wherein the parameter comprises kinematical parameters, the kinematical parameters defining movement of a third graphical object displayed separately from the first and second graphical objects during any part of a predefined time interval.

25. The method of claim 24, wherein the kinematical parameters comprise one or more of velocity, positive acceleration, negative acceleration, linear trajectory, and curved trajectory according to predefined spatial coordinate locations of the display.

26. The method of claim 1, wherein changing the display position of the first graphical object comprises changing a trajectory of the first graphical object in relation to the graphical reference marker of the second graphical object.

27. A non-transitory computer-readable storage device having computer-executable instructions stored thereon for producing interactive visuo-motor and/or interactive oculomotor non-verbal stimuli in a subject, execution of which, by a computing device, causes the computing device to perform operations comprising:
displaying a first visualization of first and second graphical objects on a display communicatively coupled with one or more processors, the first graphical object having a first color, and the second graphical object comprising a pathway having a geometric wave form and a graphical reference marker equidistant from a left and a right borderline of the pathway, wherein the pathway is defined by a parameter;
receiving, via an input device communicatively coupled with the one or more processors, command from a user to change a display position of the first graphical object, wherein the command is based on visuo-motor voluntary control of the user;
changing a display position of the first graphical object on the display according to an application of kinematical predefined rules to the command from a first display position to a second display position;
determining, on the one or more processors, a new value of the parameter based on a normalized performance score for the user, wherein the form of the pathway defined by the second graphical object changes based on the normalized performance score for the user, wherein the normalized performance score for the user is determined based on the second display position of the first graphical object relative to the graphical reference marker;

determining, on the one or more processors, a second visualization of the first and second graphical objects, based at least on the second display position of the first graphical object, and the pathway defined by the determined new value of the parameter, wherein the second visualization of the first graphical object comprises a second color of the first graphical object, the second color being selected based on an idle time of the subject compared with a predetermined idle threshold time value, the idle time being determined based on aggregation of a plurality of time gaps between arrival times of consecutive interrupts received at the one or more processors from the input device; and displaying, on the display, the second visualization of the first and second graphical object.

28. The computer-readable storage device of claim 27, the operations further comprising:

modifying the parameter during a session in accordance with the normalized performance score for the user on a previous predefined time interval.

29. The computer-readable storage device of claim 27, wherein the parameter comprises kinematical parameters configured to allow a subject's eyes to voluntarily track the graphical reference marker relative to the display position of the first graphical object.

30. The computer-readable storage device of claim 27, wherein the display position of the first graphical object is changed under visuo-motor voluntary control of the subject using a mouse.

31. The computer-readable storage device of claim 27, wherein displaying the first visualization of the first graphical object on the display comprises displaying a first graphic mobile planar object configured to move along a predefined area of the second graphical object represented as a second graphic mobile planar object.

32. The computer-readable storage device of claim 31, wherein the graphical reference marker is depicted inside the predefined area of the second graphical object.

33. The computer-readable storage device of claim 31, wherein the predefined area of the second graphical object has a graphical form of the pathway.

34. The computer-readable storage device of claim 27, wherein the first graphical object is selected from a group of graphic mobile objects comprising a car, a bird, a panther, and a yacht.

35. The computer-readable storage device of claim 27, the operations further comprising:

providing sensorial feedback information to the subject comprising a degree of navigation smoothness of the first graphical object.

36. The computer-readable storage device of claim 27, wherein the first visualization of the second graphical object comprises changes in graphical and/or kinematical parameters provided in accordance with a predefined program.

37. The computer-readable storage device of claim 27, wherein changes to a trajectory of the first graphical object comprise changes to aim the trajectory of the first graphical object to intersect the graphical reference marker of the second graphical object.

38. The computer-readable storage device of claim 27, the operations further comprising:

computing a linear distance between the first and second graphical objects, the linear distance based on a distance between a reference sign of the first graphical object and the graphical reference marker of the second graphical object.

39. The computer-readable storage device of claim 38, the operations further comprising:

computing the normalized performance score for the user during a predefined time interval using the linear distance between the first and second graphical objects during the predefined time interval.

40. The computer-readable storage device of claim 27, wherein the second graphical object defines a pathway for movement of the first graphical object.

41. The computer-readable storage device of claim 27, wherein the second graphical object is selected from a group of graphical objects comprising a road, a river, and a canyon.

42. The computer-readable storage device of claim 27, wherein changing the parameter of the geometric wave form of the pathway comprises:

changing parameters of a sinusoidal form of the pathway.

43. The computer-readable storage device of claim 27, wherein the parameter comprises graphical and kinematical parameters of the second graphical object.

44. The computer-readable storage device of claim 43, the operations further comprising:

changing the graphical and/or kinematical parameters of the second graphical object to present different difficulty levels.

45. The computer-readable storage device of claim 27, the operations further comprising:

correlating the normalized performance score for the user during a time interval with a difficulty level for the time interval; and changing a difficulty level for a subsequent time interval based on the correlation.

46. The computer-readable storage device of claim 27, wherein the graphical reference marker splits the second graphical object into equally-proportioned sides.

47. The computer-readable storage device of claim 27, wherein the graphical reference marker splits the second graphical object into differently-proportioned sides.

48. The computer-readable storage device of claim 27, wherein the first and second graphical objects are displayed during a time interval, wherein the time interval is in harmonic relationship with a day cycle.

49. The computer-readable storage device of claim 48, wherein the harmonic relationship is represented by a time interval of 84 seconds.

50. The computer-readable storage device of claim 27, wherein the parameter comprises kinematical parameters, the kinematical parameters defining movement of a third graphical object displayed separately from the first and second graphical objects during any part of a predefined time interval.

51. The computer-readable storage device of claim 50, wherein the kinematical parameters comprise one or more of velocity, positive acceleration, negative acceleration, linear trajectory, and curved trajectory according to predefined spatial coordinate locations of the display.

52. The computer-readable storage device of claim 27, wherein changing the display position of the first graphical object comprises changing a trajectory of the first graphical object in relation to the graphical reference marker of the second graphical object.

53. A system for producing interactive visuo-motor and/or interactive oculomotor non-verbal stimuli in a subject, the system comprising:

one or more processors configured to process a plurality of instructions; and a memory configured to store the plurality of instructions comprising instructions for:

displaying a first visualization of first and second graphical objects on a display communicatively coupled with one or more processors, the first graphical object having a first color, and the second graphical object comprising a pathway having a geometric wave form and a graphical reference marker equidistant from a left and a right borderline of the pathway, wherein the pathway is defined by a parameter;

receiving, via an input device communicatively coupled with the one or more processors, a command from a user to change a display position of the first graphical object, wherein the command is based on visuo-motor voluntary control of the user;

changing a display position of the first graphical object on the display according to an application of kinematical predefined rules to the command from a first display position to a second display position;

determining, on the one or more processors, a new value of the parameter based on a normalized performance score for the user, wherein the form of the pathway defined by the second graphical object changes based on the normalized performance score for the user, wherein the normalized performance score for the user is determined based on the second display position of the first graphical object relative to the graphical reference marker;

determining, on the one or more processors, a second visualization of the first and second graphical objects, based at least on the second display position of the first graphical object, and the pathway defined by the determined new value of the parameter, wherein the second visualization of the first graphical object comprises a second color of the first graphical object, the second color being selected based on an idle time of the subject compared with a predetermined idle threshold time value, the idle time being determined based on aggregation of a plurality of time gaps between arrival times of consecutive interrupts received at the one or more processors from the input device; and displaying, on the display, the second visualization of the first and second graphical objects.

54. The system of claim 53, the plurality of instructions further comprising instructions for:

modifying the parameter during a session in accordance with the normalized performance score for the user on a previous predefined time interval.

55. The system of claim 53, wherein the parameter comprises kinematical parameters configured to allow a subject's eyes to voluntarily track the graphical reference marker relative to the display position of the first graphical object.

56. The system of claim 53, wherein the display position of the first graphical object is changed under visuo-motor voluntary control of the subject using a mouse.

57. The system of claim 53, wherein displaying the first visualization of the first graphical object on the display comprises displaying a first graphic mobile planar object configured to move along a predefined area of the second graphical object represented as a second graphic mobile planar object.

58. The system of claim 57, wherein the graphical reference marker is depicted inside the predefined area of the second graphical object.

59. The system of claim 57, wherein the predefined area of the second graphical object has a graphical form of the pathway.

60. The system of claim 53, wherein the first graphical object is selected from a group of graphic mobile objects comprising a car, a bird, a panther, and a yacht.

61. The system of claim 53, the plurality of instructions further comprising instructions for:

providing sensorial feedback information to the subject comprising a degree of navigation smoothness of the first graphical object.

62. The system of claim 53, wherein the first visualization of the second graphical object comprises changes in graphical and/or kinematical parameters provided in accordance with a predefined program.

63. The system of claim 53, wherein changes to a trajectory of the first graphical object comprise changes to aim the trajectory of the first graphical object to intersect the graphical reference marker of the second graphical object.

64. The system of claim 53, the plurality of instructions further comprising instructions for:

computing a linear distance between the first and second graphical objects, the linear distance based on a distance between a reference sign of the first graphical object and the graphical reference marker of the second graphical object.

65. The system of claim 64, the plurality of instructions further comprising instructions for:

computing the normalized performance score for the user during a predefined time interval using the linear distance between the first and second graphical objects during the predefined time interval.

66. The system of claim 53, wherein the second graphical object defines a pathway for movement of the first graphical object.

67. The system of claim 53, wherein the second graphical object is selected from a group of graphical objects comprising a road, a river, and a canyon.

68. The system of claim 53, wherein changing the parameter of the geometric wave form of the pathway comprises:

changing parameters of a sinusoidal form of the pathway.

69. The system of claim 53, wherein the parameter comprises graphical and kinematical parameters of the second graphical object.

70. The system of claim 69, the plurality of instructions further comprising instructions for:

changing the graphical and/or kinematical parameters of the second graphical object to present different difficulty levels.

71. The system of claim 53, the plurality of instructions further comprising instructions for:

correlating the normalized performance score for the user during a time interval with a difficulty level for the time interval; and changing a difficulty level for a subsequent time interval based on the correlation.

72. The system of claim 53, wherein the graphical reference marker splits the second graphical object into equally-proportioned sides.

73. The system of claim 53, wherein the graphical reference marker splits the second graphical object into differently-proportioned sides.

74. The system of claim 53, wherein the first and second graphical objects are displayed during a time interval, wherein the time interval is in harmonic relationship with a day cycle.

75. The system of claim 74, wherein the harmonic relationship is represented by a time interval of 84 seconds.

76. The system of claim 53, wherein the parameter comprises kinematical parameters, the kinematical parameters defining movement of a third graphical object displayed separately from the first and second graphical objects during any part of a predefined time interval.

77. The system of claim 76, wherein the kinematical parameters comprise one or more of velocity, positive acceleration, negative acceleration, linear trajectory, and curved trajectory according to predefined spatial coordinate locations of the display.

78. The system of claim 53, wherein changing the display position of the first graphical object comprises changing a trajectory of the first graphical object in relation to the graphical reference marker of the second graphical object.

* * * * *

UNITED STATES PATENT AND TRADEMARK OFFICE
CERTIFICATE OF CORRECTION

PATENT NO. : 9,691,289 B2
APPLICATION NO. : 13/326675
DATED : June 27, 2017
INVENTOR(S) : Kullok et al.

Page 1 of 1

It is certified that error appears in the above-identified patent and that said Letters Patent is hereby corrected as shown below:

In the Claims

In Column 39, Line 6, replace "object" with --objects--.

In Column 39, Line 20, replace "the graphical" with --the first graphical--.

In Column 41, Line 21, replace "object" with --objects--.

Signed and Sealed this
Tenth Day of April, 2018

Andrei Iancu
*Director of the United States Patent and Trademark Office*